United States Patent [19]

Kelleher et al.

[11] Patent Number: 5,762,069

[45] Date of Patent: Jun. 9, 1998

[54] MULTIPLE SAMPLE BIOPSY FORCEPS

[75] Inventors: Brian S. Kelleher; Arthur C. Johnson, both of La Jolla, Calif.; Dan A. Vance, Portland, Oreg.

[73] Assignee: Akos Biomedical, Inc., San Diego, Calif.

[21] Appl. No.: 581,357

[22] Filed: Dec. 29, 1995

[51] Int. Cl.⁶ .................. A61B 10/00; A61B 17/32; A61B 17/28; A61N 1/30

[52] U.S. Cl. .......... 128/751; 128/753; 128/754; 604/19; 604/22; 606/170; 606/205; 606/206; 606/207; 606/208

[58] Field of Search .................. 128/751, 753, 128/754, 755, 757; 604/19, 22; 606/170, 171, 205, 206, 207, 208

[56] References Cited

U.S. PATENT DOCUMENTS

| | | | |
|---|---|---|---|
| 5,354,311 | 10/1994 | Kambin et al. | 606/205 |
| 5,573,008 | 11/1996 | Robinson et al. | 128/754 |
| 5,601,585 | 2/1997 | Banik et al. | 606/180 |
| 5,620,415 | 4/1997 | Lucey et al. | 604/2 |
| 5,645,075 | 7/1997 | Palmer et al. | 128/749 |

*Primary Examiner*—Vincent Millin
*Assistant Examiner*—Dinh X. Nguyen

*Attorney, Agent, or Firm*—Merle W. Richman, Esq.

[57] ABSTRACT

A flexible biopsy forceps device for acquiring more than one tissue sample comprises an elongated, flexible body having a central lumen and having a proximal end and a distal end. A control assembly is adjacent to the proximal end of the flexible body and a jaw assembly is coupled to the distal end. A jaw actuating means extends from the control assembly to the jaw assembly. The jaw assembly includes a pair of jaws that pivot from an open position to a closed position in response to movement of the jaw actuating means to surround and excise tissue samples. In their closed position, the jaw pair has a proximal opening aligned with the central lumen of the flexible body sized to allow passage of tissue samples. An intake means is disposed within the distal portion of the central lumen and may extend into the proximal opening of the jaw pair. An intake actuating means extends from the control assembly to the intake means and causes the intake means to engage a tissue sample and draw it into the lumen of the flexible body. Additional tissue samples may be excised by the jaws and serially drawn into the lumen by the intake means. At least the distal portion of the flexible body may be transparent to enable viewing of captured samples. Deflection means may be included in the device to bend the distal region toward the front of the imaging lens of an endoscope to allow observation of the intake process.

92 Claims, 8 Drawing Sheets

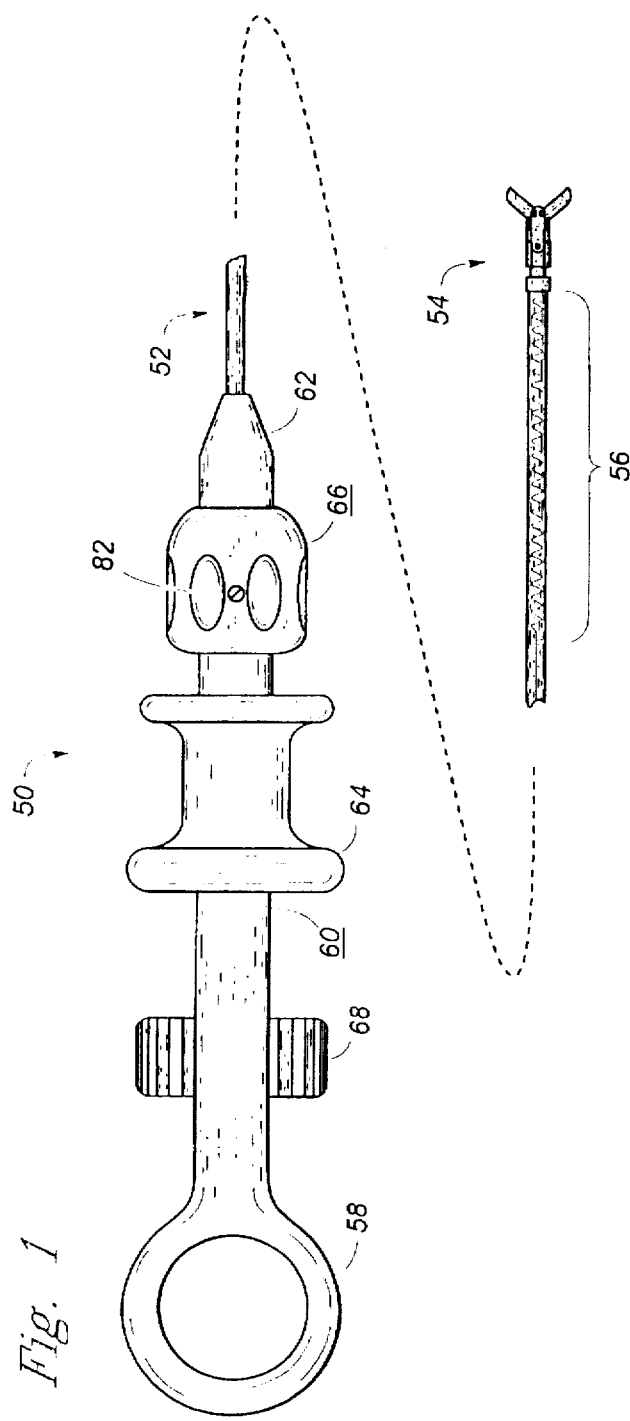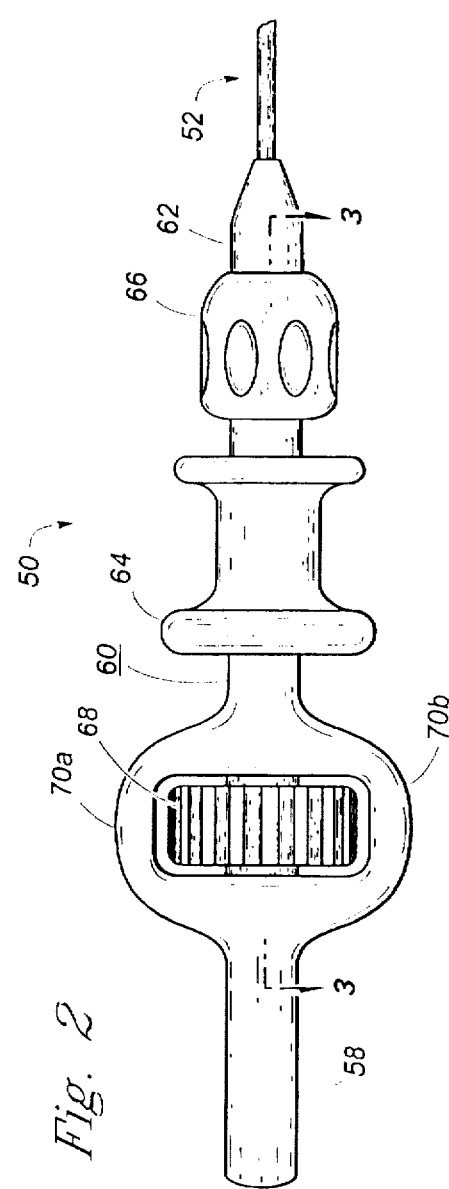

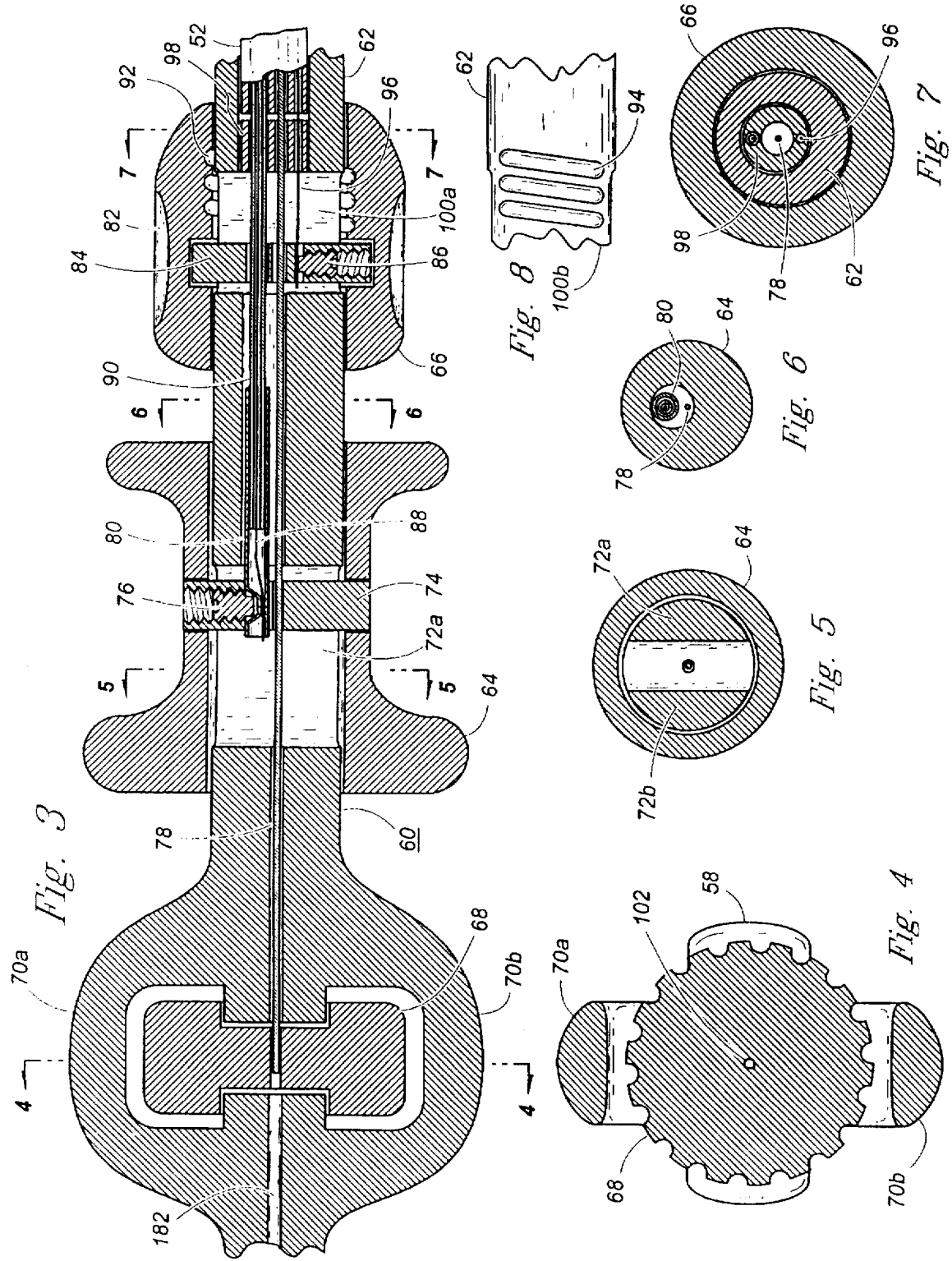

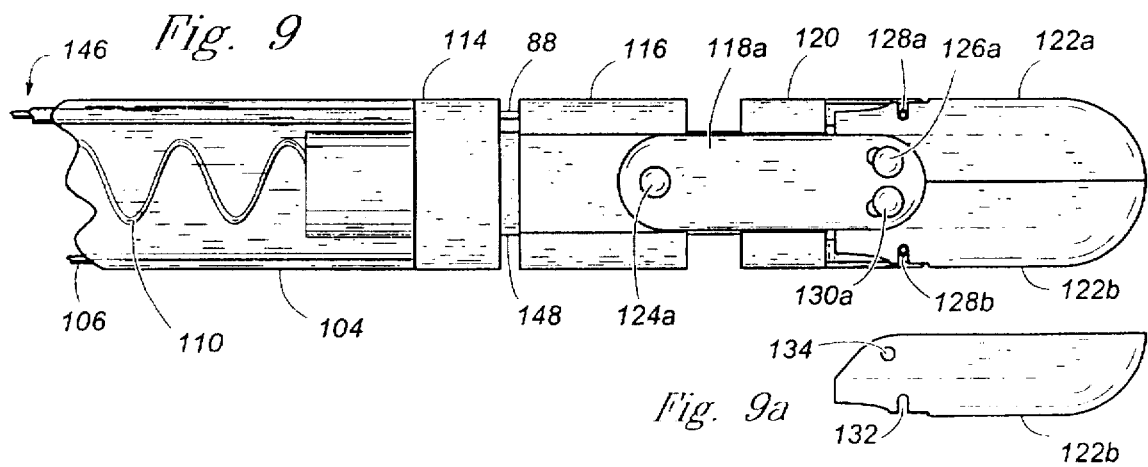
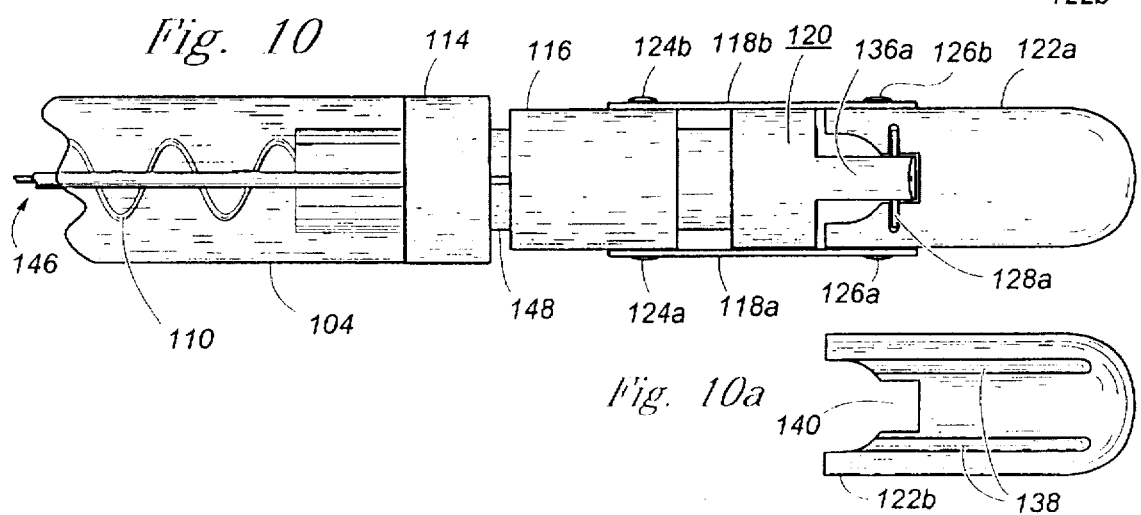
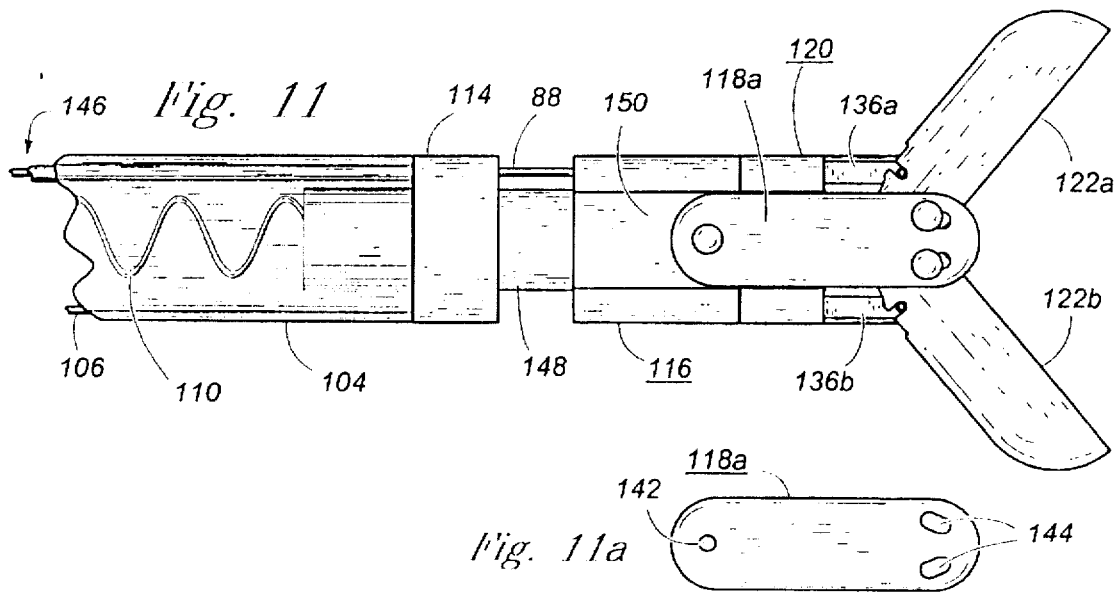

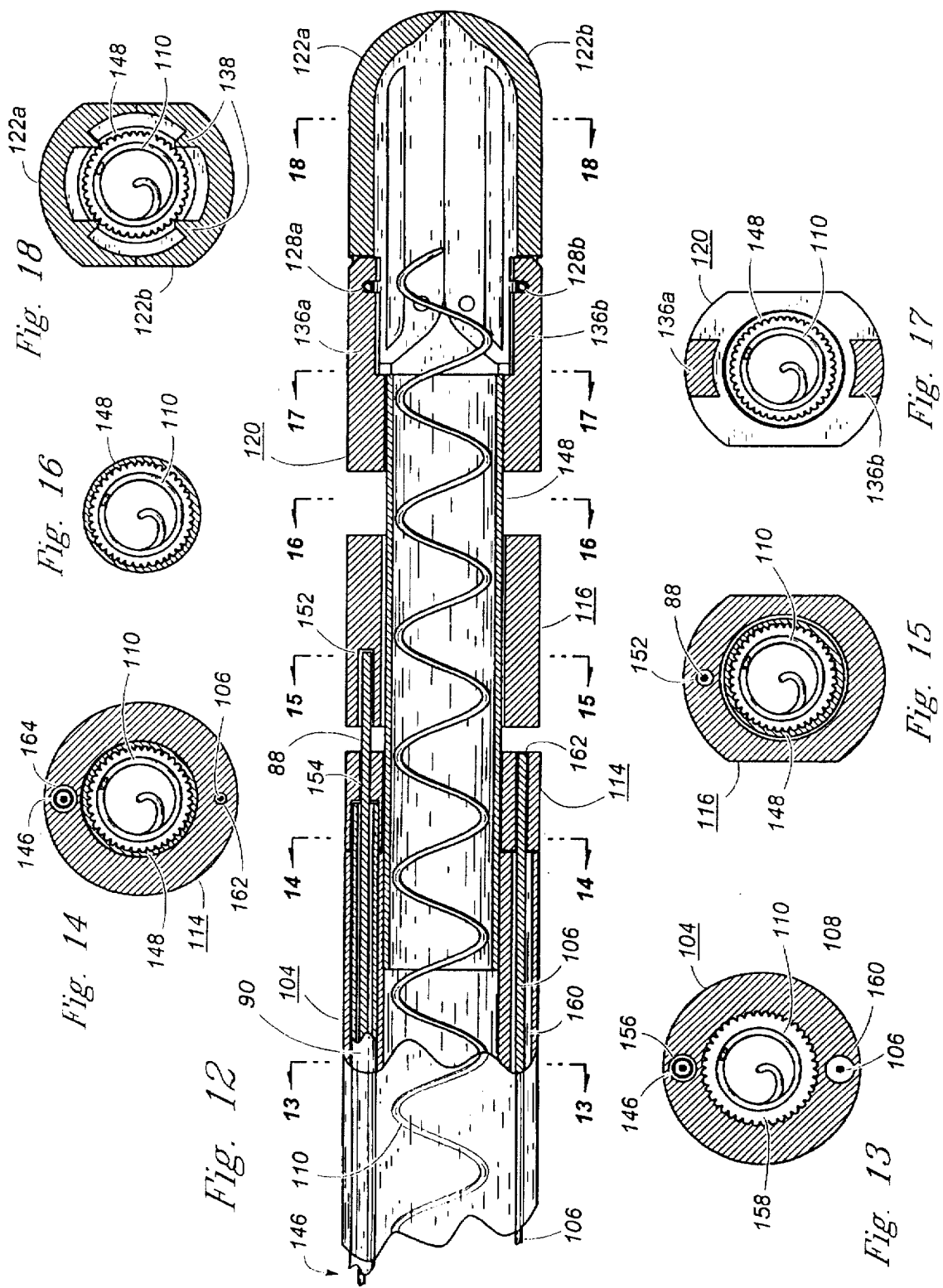

MULTIPLE SAMPLE BIOPSY FORCEPS

BACKGROUND OF THE INVENTION

1. Field of the Invention

This invention relates to medical instrumentation. More particularly, this invention relates to devices used for the retrieval of tissue samples from within a patient.

2. Description of the Prior Art

Devices used for the retrieval of tissue samples from within a patient are frequently used in conjunction with instruments such as flexible endoscopes. Such devices allow the visualization of internal structures of a patient by a clinician without the need for conventional exploratory surgery. When suspicious lesions or tissue masses are encountered during an endoscopic examination, it is helpful to excise and remove a small sample of the tissue for further analysis by a pathology laboratory.

Flexible biopsy forceps are used to perform such tissue excision and retrieval. Conventional biopsy forceps consist of an elongated, tight-wound spring-coil body with a control assembly at the proximal end and a jaw assembly at the distal end. The control assembly is typically a hand-operated push-pull mechanism that slides a control wire back and forth through the lumen of the spring-coil body. The control wire is usually attached to a pair of pivoting jaws in the jaw assembly. Pushing and pulling on the control wire opens and closes the jaws, respectively.

When used with a flexible endoscope, the forceps are inserted into the proximal opening of the forceps channel of the endoscope and advanced until the forceps appear in the field of view beyond the distal face of the endoscope. The tip of the endoscope is steered by the clinician using controls on the proximal end of the endoscope. Once the tissue of interest is aligned in front of the endoscope face, the forceps are advanced toward the tissue with the jaws open. Once the tissue is contacted, the jaws are tightly closed and the forceps are pulled back to cut and remove the tissue sample. Flexible biopsy forceps may also be used without an endoscope, as in cardiac muscle biopsy procedures. In such procedures, the flexible biopsy forceps device is inserted through a blood vessel into a heart chamber, where a sample of cardiac tissue is excised. Examples of conventional biopsy forceps are disclosed in U.S. Pat. Nos. 3,964,468 (Schulz), 4,043,323 (Komiya), 4,178,810 (Takahashi), 4,721,116 (Schingten), 4,887,612 (Esser), 4,976,723 (Schad), 5,097,728 (Cox), and 5,133,727 (Bales).

With certain types of endoscopic examinations, it is necessary to take more than one tissue sample. For example, in surveying a region of the bowel for specific disease states, it is necessary to take as many as ten to twenty tissue samples. In these instances, the use of conventional biopsy forceps is time-consuming, since the forceps must be withdrawn and re-inserted after each sample has been excised. It is often impossible to maintain the tip of the endoscope in a steady position during the removal and re-insertion of the forceps, making it difficult for the clinician to keep track of which areas have been biopsied and which have not. This can result in a frustrating and lengthy procedure for both the patient and clinician.

Several types of multiple-sample biopsy devices are known in the art. For example, U.S. Pat. No. 3,289,669 (Dwyer) discloses a biopsy capsule apparatus designed to take multiple soft tissue samples from the gastrointestinal tract without the use of an endoscope. This device includes an irrigation conduit, a tissue-cutting element, and a suction conduit to bring tissue samples out of the patient's body. This approach is bulky and complex and not adapted for use with an imaging endoscope where a clinician can carefully choose the tissue samples to be taken. Similarly, U.S. Pat. No. 3,590,808 (Muller) teaches a biopsy tool having a suction conduit for drawing soft tissue into a cup at the distal end. A pneumatically-driven knife blade cuts the tissue sample off once the tissue is in the cup. As with Dwyer '669, Muller '808 is bulky and is intended for "blind" biopsy operations without the use of an endoscope. U.S. Pat. No. 4,651,753 (Lifton) discloses a similar device, having the further refinement of a storage area in the distal tip for multiple samples. In WO 94/08512 (Thor), a multiple-sample biopsy device is disclosed which is adapted for use with an imaging endoscope. In Thor '08512, a tubular body has a slidable distal section with a side hole having a sharp cutting edge. Suction is applied at the proximal end to draw tissue into the side hole where it is cut off by slidable movement of the distal section. The tissue sample is then sucked through the lumen of the device into an external collection reservoir. As with the other multiple-sample devices discussed thusfar, Thor '08512 requires the use of an external suction source, making use of the instrument inconvenient. Also, the process of sucking the tissue sample through the lumen of the device can damage the tissue.

Other types of devices for removing multiple pieces of tissue from within a patient include rigid endoscopic tools and needle biopsy devices. Examples of rigid endoscopic tools are disclosed in U.S. Pat. Nos. 5,275,609 (Pingleton) and 5,286,255 (Weber). Pingleton '609 comprises an endoscopic device having a rigid shaft with a forceps assembly and a suction channel for removing tissue, debris and fluids. Weber '255 discloses a similar device with a central suction path and a rotating cutter at the tip. These types of devices are designed to be used independently or in conjunction with rigid endoscopes and are not readily adaptable for use with a flexible endoscope. Moreover, these devices are not intended for careful excision and removal of tissue samples without damage to the tissue.

Needle biopsy devices are designed for percutaneous extraction of tiny punch-type biopsy samples using a pointed stylet. As the stylet is pushed into a tissue mass and withdrawn, a tissue sample is collected in a notch disposed along the side of the stylet. Several designs have been adapted for multiple-sample capability, as in U.S. Pat. Nos. 4,989,614 (Dejter) and 5,195,533 (Chin). Dejter '614 teaches a device having a control assembly that includes a large-bore syringe plunger to develop a vacuum source. The vacuum is used to draw biopsy samples through the needle to a collection chamber in the control assembly. Chin '533 uses a notched stylet similar to conventional designs, except the notch length is long enough to hold several samples. Needle biopsy devices, however, are not as suitable for taking large samples of tissue from regions such as the mucosal wall of the gastrointestinal tract, as are conventional biopsy forceps.

There is, therefore, a need for a flexible biopsy forceps device capable of retrieving more than one tissue sample from within a patient. Preferably, such a device may be used with a conventional imaging endoscope. It is desirable for such a device to be self-contained and not require connection to a suction source or pressurized fluid source. In addition, it is desirable for a clinician to be able to observe the jaw closure process and the movement of tissue samples into a collection area. Also, it is preferable for the collected samples to be of a size comparable to those obtained from conventional biopsy forceps devices, and for such samples to be easily removed from the device. It is further desirable for such a device to be relatively inexpensive and easy to use.

SUMMARY OF THE INVENTION

In accordance with the present invention, there is provided a flexible biopsy forceps device for acquiring more than one tissue sample, comprising an elongated, flexible body having a central lumen and having a proximal end and a distal end. A control assembly is adjacent to the proximal end of the flexible body and a jaw assembly is coupled to the distal end. A jaw actuating means extends from the control assembly to the jaw assembly. The jaw assembly includes a pair of jaws that pivot from an open position to a closed position in response to movement of the jaw actuating means to surround and excise tissue samples. In their closed position, the jaw pair has a proximal opening aligned with the central lumen of the flexible body sized to allow passage of tissue samples. An intake means is disposed within the distal portion of the central lumen and may extend into the proximal opening of the jaw pair. An intake actuating means extends from the control assembly to the intake means and causes the intake means to engage a tissue sample and draw it into the lumen of the flexible body. Additional tissue samples may be excised by the jaws and serially drawn into the lumen by the intake means. At least the distal portion of the flexible body may be transparent to enable viewing of captured samples. Deflection means may be included in the device to bend the distal region toward the front of the imaging lens of an endoscope to allow observation of the intake process.

The jaw assembly comprises a pair of cupped jaws having at least one edge adapted to clamp or cut tissue samples. The jaw shape and hinging arrangement are configured to form a proximal opening through the center of the jaw assembly, at least during jaw closure. This opening is large enough to allow the passage of tissue samples without damage to the tissue.

The intake means comprises an element or assembly adapted to engage the proximal end of a captured tissue sample an draw it into the lumen of the flexible body. In the preferred embodiment, the intake means is a helical coil having an outer diameter slightly less than the diameter of the proximal opening of the jaw assembly. The helical coil is disposed within the lumen of the flexible body and may extend for a length proportional to the sample collection capacity of the device. The intake actuating means in the preferred embodiment is a torquable shaft connected to the proximal end of the helical coil, such that rotation of the torquable shaft causes rotation of the helical coil. As the helical coil is rotated, the distal tip wraps around the proximal end of the tissue sample. Ribbed walls inside the jaws prevent the tissue sample from rotating. As a result, the screw-action of the rotating helical coil draws the tissue samples proximally into the lumen of the flexible body. The flexible body may also have longitudinal ribs on its inner surface to prevent rotation of the tissue sample.

Other types of intake means are readily conceivable. For example, a flexible, thin-wall tube having an inner surface with hair-like barbs projecting proximally could be used. By pushing the tube into the proximal opening of the jaw assembly, a tissue sample could be forced inside the tube where it would become engaged by the hair-like projections. Similarly, a harpoon-type needle could be disposed within the lumen of the flexible body, configured to advance into the jaw opening and engage a tissue sample.

The control assembly comprises a push-pull mechanism to slide the jaw actuating means back and forth through a lumen of the flexible body, thereby opening and closing the jaws. The control assembly also includes an intake actuating control to manipulate the intake actuating means, in order to move the intake means so as to engage a tissue sample. In the preferred embodiment, the intake actuating control is a knurled wheel. An optional feature in the preferred embodiment is an access hole in the control assembly allowing a tool to push on the proximal end of the torquable shaft so as to eject the helical coil out of the mouth of the open jaws, along with tissue samples engaged upon the coil.

Another aspect of the preferred embodiment is the construction of the flexible body of the device. In conventional biopsy forceps devices, the flexible body is typically a tight-wound spring-coil having a lumen through which a control wire extends. In a conventional design, actuation of the jaw assembly is accomplished by tensioning the control wire relative to the spring-coil. The spring-coil body is laterally flexible, yet provides a substantially incompressible column support between the control assembly and the jaw assembly. Such a spring-coil design is non-ideal for a multiple sample biopsy forceps device because the wall is not transparent, thus preventing the clinician from observing the intake process. A clear, flexible tube is preferable—however, such a tube would buckle under the compressive forces exerted by tensioning the jaw actuating wire. In the preferred embodiment, this problem is solved by the use of a coaxial actuating assembly that is disposed along the wall of a clear, flexible tube. The coaxial actuating assembly is described in detail in co-pending and commonly-owned U.S. Patent Application "Flexible Forceps Device" which is included herein in its entirety by reference thereto. The coaxial actuating assembly comprises a flexible hollow tube, preferably stainless steel, with a control wire extending therethrough. This assembly bears both the tension and compression forces exerted during jaw actuation, so the clear, flexible tube bears no load.

Another feature of the preferred embodiment relates to deflection of the distal region. In a typical front-viewing endoscope, the opening of the forceps channel on the distal face of the endoscope is relatively close to the imaging lens. This gives the clinician a view of the forceps similar to the view one would have of a rod projecting straight out from one's forehead. Thus, even if the flexible body of the forceps is transparent, the clinician still cannot get a good view of the intake process or of the captured samples. In the preferred embodiment, a deflection means is included to enable the clinician to bend the distal region across the face of the endoscope so the intake process and captured samples can be adequately observed.

The deflection means employed may comprise a deflection wire disposed in a small lumen in the wall of the flexible body, on the side opposite the coaxial actuating assembly. Pulling on the deflection wire causes the distal region to bend toward the deflection wire. Alternatively, the coaxial actuating assembly may be slidably disposed in a lumen in the wall of the flexible body and used as a pushable element to cause the distal region to deflect away from the side with the coaxial actuating assembly. With this arrangement, restraining means may be disposed along the flexible body to prevent it from stretching or to confine stretching to a specific bending region. These types of deflection schemes, and others, are disclosed in co-pending and commonly-owned U.S. Patent Application "Steerable, Flexible Forceps Device" incorporated herein in its entirety by reference thereto.

The preferred embodiment may be further refined to incorporate torsional-stiffening means disposed along the flexible body to enable the clinician to control the radial orientation of the distal region by rotating the proximal end of the flexible body.

It is among the general objects of the present invention to provide a flexible biopsy forceps device capable of retrieving more than one tissue sample from within a patient.

It is another object of the invention to provide a multiple-sample flexible biopsy forceps device for use with a flexible endoscope.

Yet another object of the invention is to provide a multiple-sample flexible biopsy forceps device that is self-contained and does not require connection to a suction source or pressurized fluid source.

A further object of the invention is to provide a multiple-sample endoscopic biopsy forceps device adapted so that a clinician may observe the jaw closure process and the movement of tissue samples into a collection area.

Another object of the invention is to provide a multiple-sample flexible biopsy forceps device capable of collecting tissue samples of a size comparable to those obtained from conventional biopsy forceps devices.

It is a further object of the invention to provide a multiple-sample flexible biopsy forceps device having a means for easily removing the collected samples from the device.

Yet another object of the invention is to provide a multiple-sample flexible biopsy forceps device that is relatively inexpensive and easy to use.

BRIEF DESCRIPTION OF THE DRAWINGS

The foregoing and other objects and advantages of the invention will be appreciated more fully from the following further description thereof, with reference to the accompanying drawings wherein:

FIG. 1 shows a side view of the preferred embodiment, with a portion of the flexible body omitted for brevity, as indicated by the dotted line;

FIG. 2 is a top view of the control assembly depicted in FIG. 1;

FIGS. 3 through 7 are enlarged sectional views of portions of the embodiment illustrated in FIG. 2;

FIG. 8 is an enlarged view of a portion of the embodiment depicted in FIG. 3;

FIG. 9 is an enlarged side view of the jaw assembly from the preferred embodiment, showing the jaws in their closed position;

FIG. 9a is an enlarged side view of the lower jaw from the embodiment illustrated in FIG. 9;

FIG. 10 is an enlarged top view of the jaw assembly from the preferred embodiment, showing the jaws in their closed position;

FIG. 10a is an enlarged top view of the lower jaw from the embodiment illustrated in FIG. 10;

FIG. 11 is an enlarged side view of the jaw assembly from the preferred embodiment, showing the jaws fully open;

FIG. 11a is an enlarged side view of an actuator arm from the embodiment illustrated in FIG. 11;

FIG. 12 is an enlarged side view of the distal region of the preferred embodiment, with portions broken away to reveal underlying structures;

FIGS. 13 through 18 illustrate enlarged sectional views of the embodiment shown in FIG. 12;

DESCRIPTION OF THE PREFERRED EMBODIMENTS

Figure 19:
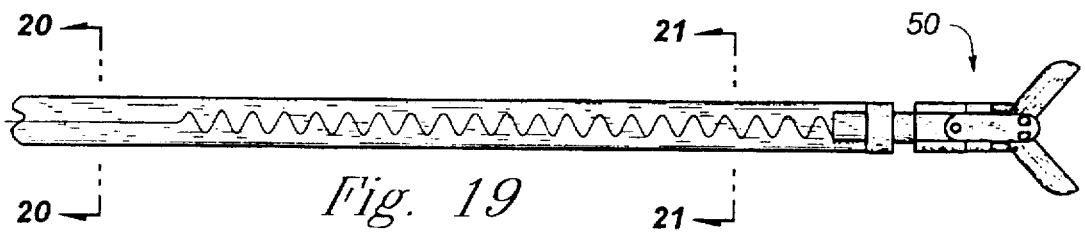
FIG. 19 is a side view of the distal region of an alternative embodiment in accordance with the present invention.

FIG. 1 illustrates a side view of the preferred embodiment comprising control assembly 50, jaw assembly 54 and flexible body 52. Control shaft 60 has thumb ring 58 disposed at its proximal end and interface region 62 disposed at its distal end. Finger spool 64 is slidably disposed around a central portion of control shaft 60 for controlling jaw actuation. Collar 66 is rotatably disposed about control shaft 60 for controlling deflection of the distal region. Fingertip dimples 82 are radially disposed about collar 66 to enhance gripping. Flexible body 52 is anchored to control assembly 50 in interface region 62. A portion of flexible body 52 has been omitted for brevity, as indicated by the dotted line. The distal region of flexible body 52 comprises sample collection region 56. Jaw assembly 54 is attached to the distal end of flexible body 52.

FIG. 2 is a top view of control assembly 50, showing the bifurcation of control shaft 60 into struts 70a and 70b to capture wheel 68. Rotation of wheel 68 causes rotation of the intake actuating means, or drive shaft 78 (shown in FIG. 3). Control assembly 50 is adapted for two-handed use by an operator. A first thumb is inserted into thumb ring 58 and the forefinger and middle finger of the same hand fork around the concave region of finger spool 64. Thus, squeezing together and spreading apart the thumb and fingers of that hand causes slidable movement of finger spool 64 along control shaft 60. Wheel 68 and collar 66 can be selectively rotated by the forefinger and thumb of the opposite hand. Control shaft 60, including thumb ring 58, struts 70a and 70b, and interface region 62 are preferably molded as a unitary element from a high-impact plastic resin such as ABS (acrylonitrile-butadiene-styrene) or the like. Wheel 68, finger spool 64 and collar 66 may also be molded from a resin such as ABS or the like, although each of these parts is preferably molded as two joinable halves to ease the process of putting together control assembly 50.

FIG. 3 is an enlarged, sectional view of a portion of the control assembly illustrated in FIG. 2. The proximal end of flexible body 52 is fixedly disposed within the distal end of interface region 62, using adhesive bonding or the like. Proximal anchor 98, which may be formed from metal such as brass, is attached to the bore of interface region 62 by press-fitting, adhesive bonding or the like. Hollow tube 90 is fixedly anchored to proximal anchor 98 by means such as welding, brazing, soldering, adhesive bonding or the like. An aperture in proximal anchor 98 allows slidable passage of steering wire 96 and drive shaft 78, as best seen in FIG. 7. It will be appreciated that proximal anchor 98 may be eliminated by incorporating an analogous anchoring region for hollow tube 90 directly into interface region 62. Hollow tube 90 extends beyond proximal anchor 98 to be slidably received by the lumen of outer sleeve 80. In the preferred embodiment, hollow tube 90 is made from stainless steel tubing having an outer diameter in the range of about 0.006 to 0.020 inches and an inner diameter in the range of about 0.004 to 0.016 inches.

Finger spool 64 is slidably disposed along control shaft 60. Cross-bar 74 extends across the center of finger spool 64 and is guided and restrained by forked elements 72a and 72b, illustrated in FIG. 5. Cross-bar 74, preferably fabricated from metal such as brass, has a blind, internally-threaded bore on one end to receive set screw 76. A first transverse hole in cross-bar 74 is located at the end of the threaded bore. Outer sleeve 80 enshrouds control wire 88 and the proximal end of hollow tube 90. Outer sleeve 80 is disposed into the first transverse hole of cross-bar 74 such that advancement of set screw 76 will secure outer sleeve 80 and control wire 88 within the first transverse hole. Outer sleeve 80 is preferably fabricated from metal tubing such as stainless steel. As best seen in FIG. 6, the central bore of control shaft 60 slidably receives the distal end of outer sleeve 80, allowing free longitudinal movement of outer sleeve 80 within the bore, but relatively little lateral movement. The length of outer sleeve 80 is chosen such that at the proximal-most position of finger spool 64, hollow tube 90 remains within the lumen of outer sleeve 80. With this configuration, control wire 88 is always surrounded by a tubular element, thereby preventing any deformative buckling that could occur when cross-bar 74 pushes on control wire 88. Control wire 88 is preferably made of stainless steel wire having a diameter in the range of about 0.002 to 0.012 inches. A second transverse hole in cross-bar 74 allows for slidable passage of drive shaft 78. Drive shaft 78 must be laterally flexible but torsionally rigid such that rotational motion at the proximal end will cause rotation of the distal end. Drive shaft 78 may be fabricated from stainless steel tubing having an outer diameter in the range of about 0.006 to 0.016 inches and an inner diameter on the order of about 0.004 to 0.012 inches. Alternatively, drive shaft may be formed as an extruded rod or tube including one or more torsional-stiffening layers such as braided flat-wire, as is well known in the art.

Rotating collar 66 has a roughly cylindrical shape, as best seen in FIGS. 3 and 7. Along the central portion of the inside surface of collar 66 is disposed an annular groove sized to slidably capture cross-bar 84. Along the distal portion of the inside surface of collar 66 are disposed a set of continuous female threads 92. Female threads 92 are sized to mate with segments of male threading 94 which are disposed upon the outer surfaces of forked elements 100a and 100b, as can be seen in FIG. 8. Referring to FIG. 3, cross-bar 84 is guided and restrained by forked elements 100a and 100b. Cross-bar 84, preferably fabricated from metal such as brass, has a blind, internally-threaded bore on one end to receive set screw 86. A first transverse hole in cross-bar 84 is located at the end of the threaded bore. Steering wire 96 is disposed into the first transverse hole of cross-bar 84 such that advancement of set screw 86 will secure steering wire 96 within the transverse hole. A second transverse hole in cross-bar 84 allows free passage of hollow tube 90. As collar 66 is rotated, it advances along its threads either distally or proximally, forcing cross-bar 84 to move distally or proximally, respectively. In this manner, rotation of collar 66 causes pushing or pulling on steering wire 96. It will be appreciated that a tubular constraint similar to outer sleeve 80 may be disposed around the unconstrained length of steering wire 96 to prevent buckling, if necessary. A third transverse hole in cross-bar 84 allows free passage of drive shaft 78.

Wheel 68 is captured by axial hubs molded into control shaft 60 and is surrounded by struts 70a and 70b. As best seen in FIG. 4, wheel 68 preferably has ridges or knurls to allow better gripping. Hole 102 is disposed through the central axis of wheel 68 and preferably has an off-round shape such as a D-shape. Drive shaft 78 extends proximally beyond cross-bar 74 through a small bore in control shaft 60 and is tightly received by hole 102 of wheel 68. Preferably, the proximal end of drive shaft 78 has an off-round shape to match that of hole 102, such that turning of wheel 68 will impart rotational movement to drive shaft 78 without allowing drive shaft 78 to slip within hole 102. Access hole 182 extends proximally through control shaft 60 in line with drive shaft 78 and continues through the proximal edge of thumb ring 58 (not shown). Access hole 182 allows a small-diameter tool to be inserted and pushed distally to apply pressure on the proximal end of drive shaft 78. As will be described later, this allows ejection of the stored tissue samples from the distal end of the device.

FIGS. 9 through 11 show enlarged views of the distal region of the device. Extruded tube 104, the main component of flexible body 52, is preferably fabricated from a flexible, transparent material such as polyurethane, PVC (polyvinyl chloride) or the like. Extruded tube 104 may be subjected to a surface modification or coating process to improve lubricity in order to ease the process of insertion through an endoscope channel or circulatory vessel. Surface modifications to improve lubricity include gas plasma treatment (Polar Materials/Wheaton, Inc., Pennsville, N.J.), ion beam deposition (Spire Corporation, Bedford, Mass.) and the like. Lubricious coatings include parylene (Advanced Surface Technology, Inc., Billerica, Mass.), fluoropolymer (Advance Coating Technology, Mechanicsburg, Pa.), various hydrogels (BSI Corporation, Eden Prairie, Minn.) and the like. In the preferred embodiment, at least the distal region of extruded tube 104 is optically transparent to allow the clinician to view the sample collection process. The outer diameter of extruded tube 104 is a function of the type of device being fabricated, since different size devices are used for different procedures. By way of example only, the outer diameter of extruded tube 104 may be in the range of about 0.030 to 0.12 inches.

Coaxial actuating assembly 146 and steering wire 106 extend through lumina in the wall of extruded tube 104. Helical coil 110 extends through the central lumen of extruded tube 104 and through connecting tube 148. The distal end of extruded tube 104 fits tightly around the proximal end of connecting tube 148 and is affixed thereto by an adhesive such as silicone, polyurethane, cyanoacrylate or the like. Bulkhead 114 is affixed to connecting tube 148 by means of adhesive bonding, soldering, brazing, welding or the like. Sliding actuator 116 is slidably disposed about the mid-section of connecting tube 148. Control wire 88 extends through bulkhead 114 and is anchored in sliding actuator 116. Sliding actuator has flatted sides 150 on which are anchored actuator arms 118a and 118b by means of riveted hinge-pins 124a and 124b, respectively. Actuator arms 118a and 118b are coupled to jaws 122a and 122b by means of riveted hinge-pins 126a, 126b, 130a and 130b (not shown). These hinge-pins extend through holes 134 of each jaw, as best seen in FIG. 9a, and may be fabricated from stainless steel or the like. Jaws 122a and 122b pivot about hinge-pins 128a and 128b. Hinge-pins 128a and 128b extend through under-cut grooves in beams 136a and 136b of jaw support 120, and are affixed in outer grooves 132 of each jaw, as best seen in FIGS. 9a and 10. Hinge-pins 128a and 128b are preferably affixed to outer grooves 132 by means of welding, brazing or the like. Hinge-pins 128a and 128b may be fabricated from stainless steel wire or the like, having a diameter in the range of 0.003 to 0.010 inches, depending upon the desired hinge strength and the size of the particular device. In the preferred embodiment, hinge-pins 128a and 128b have a diameter of about 0.005 inches. Jaw support 120 is affixed to connecting tube 148 by means of adhesive bonding, soldering, brazing, welding or the like.

As shown in FIG. 10a, each jaw has a proximal cutout 140. Cutout 140 has a substantially square distal section to snugly fit around beams 136a and 136b. Cutout 140 also has a rounded portion sized so that when jaws 122a and 122b are in their open position, the proximal portion of each jaw does not encumber the distal tip of helical coil 110. Each jaw also has a pair of fins 138 aligned with the long axis of the device. Fins 138 are adapted to project inwardly from the inner surface of each jaw in order to hold tissue samples in place.

In FIG. 9, jaws 122a and 122b are in their closed position. By pushing in a distal direction on control wire 88, sliding actuator 116 moves distally, forcing both actuator arms 118a and 118b to move distally, which applies a distal force on riveted hinge-pins 126a, 126b, 130a and 130b (not shown), thereby pushing open jaws 122a and 122b, as illustrated in FIG. 11. As shown in FIG. 11a, actuator arms 118a and 118b each have a proximal hole 142 for receiving hinge-pins 124a and 124b, and guide channels 144 for receiving riveted hinge-pins 126a, 126b, 130a and 130b (not shown). Guide channels 144 are angled to allow for a change in spacing during jaw opening between riveted hinge-pins 126a and 130a and between riveted hinge-pins 126b and 130b.

FIGS. 12 through 18 show detailed views of the distal region of the device, with portions removed to reveal underlying structure. Extruded tube 104 is attached to connecting tube 148 and abuts bulkhead 114. Helical coil 110 extends through central lumen 158 of extruded tube 104 and through connecting tube 148 into the proximal region of the interior of jaws 122a and 122b. The length of helical coil 110 depends upon the desired length of the sample storage area within the lumen of extruded tube 104. In the preferred embodiment, helical coil 110 is between one-half and six inches long. Helical coil 110 is preferably made from stainless steel wire having a diameter in the range of about 0.002 to 0.016 inches. The wire used to form helical coil 110 may have a round, square or similar profile and may be coated or otherwise treated to reduce friction. Coaxial actuating assembly 146, consisting of control wire 88 and hollow tube 90, extends through lumen 156 in the wall of extruded tube 104, as best seen in FIG. 13. In the preferred embodiment, lumen 156 has a diameter on the order of about 0.007 to 0.024 inches, and coaxial actuating assembly 146 is affixed therein by a flexible adhesive such as silicone, urethane or the like. Alternatively, coaxial actuating assembly 146 may be disposed along the outside of extruded tube 104, or adhesively disposed along a channel or slit in the wall of extruded tube 104. A further option is to capture coaxial actuating assembly 146 between the outside of extruded tube 104 and an outer layer which may be applied by coating, heat-shrinking or the like.

As shown in FIG. 13, central lumen 158 preferably has longitudinal ribs disposed radially along its inner surface. These ribs act to prevent rotational movement of tissue samples within lumen 158 as helical coil 110 is rotated, while presenting relatively little resistance to longitudinal movement of tissue samples. The diameter of lumen 158 will depend upon the application, since the outer diameter of the device and the desired size of tissue samples may vary. By way of example only, lumen 158 may have a diameter in the range of about 0.02 to 0.10 inches. Connecting tube 148 has similar longitudinal ribs disposed along its inner surface, as best seen in FIG. 16. Connecting tube 148 may be fabricated from standard, thin-wall stainless steel tubing, using a secondary operation to create the ribs. The outer surface of the mid-section of connecting tube 148, upon which sliding actuator 116 slides, is preferably highly polished or otherwise treated to reduce friction. The length of connecting tube 148 is chosen to allow adequate connection to extruded tube 104, mounting of bulkhead 114 and jaw support 120, and enough length in the mid-section for sliding actuator 116 to be able to fully actuate the jaws. The outer diameter of connecting tube 148 will vary with the product application, but is preferably in the range of about 0.02 to 0.10 inches.

As best seen in FIGS. 12 and 14, hollow tube 90 of coaxial actuating assembly 146 is fixedly anchored in hole 164 of bulkhead 114. Referring to FIGS. 12 and 15, control wire 88 extends past the distal end of hollow tube 90 through aperture 154, which has a substantially smaller diameter than hole 164, and is fixedly anchored in hole 152 within sliding actuator 116. Steering wire 106 extends through lumen 160 of flexible tube 104 and is anchored in hole 162 of bulkhead 114, as shown in FIG. 14. The inner surface of lumen 160 and the surface of steering wire 106 may be coated or otherwise treated to reduce friction. In the preferred embodiment, steering wire 106 is made of stainless steel and has a diameter in the range of about 0.002 to 0.016 and has a Teflon coating. Anchoring of hollow tube 90, control wire 88 and steering wire 106 may be done by soldering, brazing, welding, adhesive bonding or the like.

Bulkhead 114 is preferably made from stainless steel, either by machining stainless steel tubing or by a process such as investment casting, powder metallurgy or metal injection molding. Bulkhead 114 preferably has an outer diameter close to that of extruded tube 104 and a width in the range of about 0.015 to 0.10 inches. Sliding actuator 116 is also preferably fabricated from stainless steel and has an outer diameter close to that of extruded tube 104 and has a width on the order of about 0.015 to 0.10 inches. The inside diameter of sliding actuator 116 is preferably slightly larger than the outer diameter of connecting tube 148 and is preferably highly polished or otherwise treated to reduce friction. Sliding actuator 116 may be fabricated either by machining stainless steel tubing or by a process such as investment casting, powder metallurgy or metal injection molding.

Jaw support 120 has a tubular proximal portion and a pair of distal beams 136a and 136b, as best seen in FIGS. 12 and 17. The outer diameter of jaw support is close to that of extruded tube 104. In the preferred embodiment, beams 136a and 136b have a length of about 0.06 inches and a width of about 0.030 inches, although these dimensions can be scaled up or down for different product applications. Jaw support 120 is preferably made from stainless steel, either by machining stainless steel tubing or by a process such as investment casting, powder metallurgy or metal injection molding.

FIGS. 12 and 18 show details of jaws 122a and 122b. The sides of each jaw are flatted to match the sides of sliding actuator 116, thereby providing co-planar surfaces for actuator arms 118a and 118b to straddle. In their closed position, jaws 122a and 122b preferably have an outer diameter close to that of extruded tube 104. The outer, distal regions of the jaws preferably have a smooth, rounded shape to ease the process of insertion into an endoscope or vessel. Fins 138 project inwardly to prevent tissue samples from rotational movement when helical coil 110 is rotated, while presenting relatively little resistance to longitudinal movement of the tissue samples. The distal rim of at least one of jaws 122a and 122b may be sharpened to promote cutting of tissue (as indicated by cutting edge 166 in FIG. 22). The proximal segments of the rim, adjacent to holes 134 (refer to FIG. 9a), are curved and flattened to provide a rocker bearing during opening and closing of the jaws. Jaws 122a and 122b are preferably made from stainless steel, either by machining from stainless steel stock, or by a process such as stamping, investment casting, powder metallurgy or metal injection molding.

In the preferred embodiment, tensioning steering wire 106 applies a compressive force to the entire length of extruded tube 104. The wall of extruded tube 104 opposite steering wire 106 is relatively incompressible since coaxial actuating assembly 146 is adhesively disposed within that wall. As a result, the entire length of extruded tube 104 deflects toward the steering wire side. However, it is preferable for the deflection to be confined to the distal region of the device. Fortunately, when the main length of the device is radially constrained by the walls of an endoscope channel, only the portion of extruded tube 104 that extends past the distal tip of the endoscope can deflect. In certain situations, however, such as when the device is used with small-diameter endoscopes, it may be desirable to mechanically restrict the deflection to the distal region without having to rely on a radial constraint.

Figure 20A:
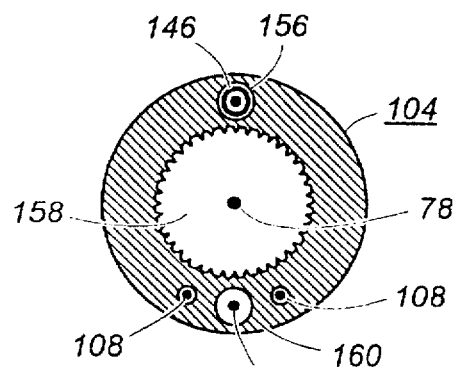
FIGS. 20a and 21a show enlarged sectional views of the embodiment illustrated in FIG. 19.
Figure 21A:
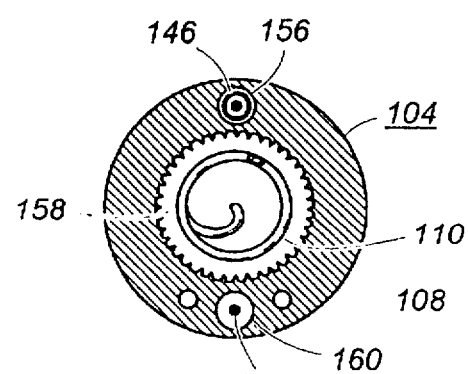

FIGS. 19, 20a through 20c, and 21a through 21c show the distal region of alternative embodiments adapted to confine deflection to the distal region of the device. In FIGS. 20a and 21a, the construction of extruded tube 104 is substantially equivalent to the previously-described embodiment, except two additional lumina have been added in the wall to accommodate restraining filaments 108. Restraining filaments 108 extend from control assembly 50 to the proximal end of the intended bending region. The filaments may be embedded in the wall of extruded tube 104 or may be bonded into lumina in the wall or they may be attached to anchor members in or upon extruded tube 104. Steering wire 106 functions as a push-rod to cause the distal region of extruded tube 104 to undergo tension. Since the side of extruded tube 104 in which coaxial actuating assembly 146 is disposed is restrained from stretching, the applied tension results in stretching of the steering wire side, thus leading to deflection toward the coaxial actuating assembly side. Restraining filaments 108 prevent the main length of extruded tube 104 from undergoing deflection since they prevent stretching on the steering wire side except in the distal region. Restraining filaments 108 may be fabricated from wire, rod, tube, strip, cord or other materials having both adequate flexibility and the strength to support the maximum tensile load for the particular application.

Figure 20B:
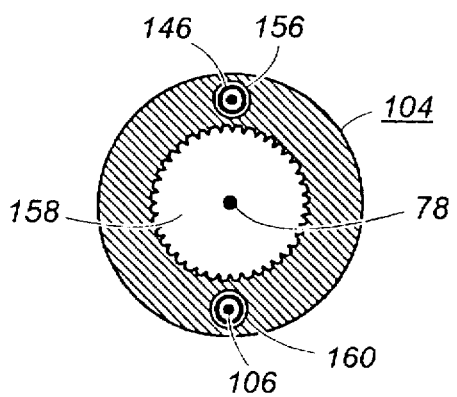
FIGS. 20b and 21b show enlarged sectional views of an embodiment similar to that illustrated in FIG. 19, having an alternative deflection mechanism.
Figure 21B:
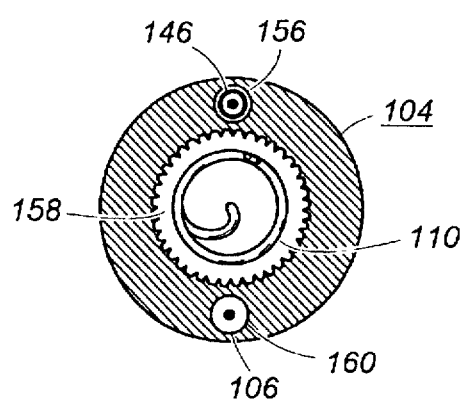

FIGS. 20b and 21b show an alternative embodiment where in a flexible, thin-wall tube is disposed around steering wire 106 in lumen 160. The hollow tube provides a relatively incompressible column support around steering wire 106. The hollow tube extends from control assembly 50 to the proximal end of the intended bending region and is fixedly disposed within lumen 160 by a flexible adhesive. Steering wire 106 extends from control assembly 50 through the hollow tube to bulkhead 114, leaving the distal length of steering wire 106 unsupported. Control assembly 50 is adapted to pull on steering wire 106 relative to the hollow tube. As steering wire 106 is tensioned, the hollow tube surrounding steering wire 106 prevents the main length of extruded tube 104 from undergoing compression. Therefore, only the distal region of extruded tube 104 undergoes compression. Because coaxial actuator 146 is disposed within the opposite wall and is essentially incompressible, the distal region is forced to deflect toward the steering wire side.

Figure 20C:
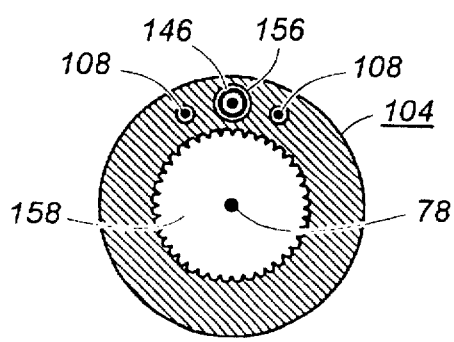
FIGS. 20c and 21c show enlarged sectional views of an embodiment similar to that illustrated in FIG. 19, having an alternative deflection mechanism.
Figure 21C:
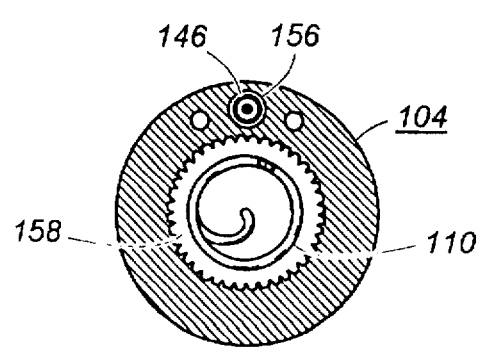

A different embodiment is illustrated in FIGS. 20c and 21c. In this embodiment, the steering wire has been eliminated. Instead, coaxial actuating assembly 146 is slidably disposed within lumen 156 and functions as a push-rod to cause deflection of the distal region. The diameter of lumen 156 is preferably 0.002 to 0.01 inches greater than the outer diameter of coaxial actuating assembly 146 in order to allow room for sliding. In addition, the inner surface of lumen 156 and the outer surface of coaxial actuating assembly 146 may be coated or otherwise treated to reduce friction. Restraining filaments 108 are disposed in the wall of extruded tube 104 near lumen 156 and extend from control assembly 50 to the proximal end of the intended bending region. The filaments may be embedded in the wall of extruded tube 104 or may be bonded into lumina in the wall or they may be attached to anchor members in or upon extruded tube 104. Control assembly 50 is adapted to push on coaxial actuating assembly 146 relative to extruded tube 104, thereby placing extruded tube 104 in tension. Restraining filaments 108 prevent the main length of extruded tube 104 from stretching in response to the applied tension. As a result, only the distal region is exposed to tension. The coaxial actuator side stretches more than the opposite side since it is closest to the source of the tension, thus resulting in deflection of the distal region away from the coaxial actuating side.

In addition to controlling deflection, it may also be desirable to control the radial orientation of the distal end of the device. Such control not only allows better positioning of the distal region for observation purposes, but may also assist in positioning the jaws for taking tissue samples from hard-to-reach places within a body cavity. In order to transmit rotational movement from control assembly 50 to the distal region, torsional-stiffening means must be disposed along the length of flexible body 52. Otherwise, flexible body 52 may twist upon itself or may undergo unpredictable wind-up and whiplash. A torsional-stiffening layer may be constructed using techniques and materials well known to those skilled in the art. For example, a torque layer may added to flexible body 52. The torque layer may be comprised of helically-wrapped wire or cord, secured within or around flexible body 52. Securing may be done by bonding the cord to extruded tube 104 with a flexible adhesive such as epoxy or urethane, or by tightly capturing the cord between an outer layer of heat-shrink tubing and extruded tube 104. Alternatively, a separate outer layer of flexible polymer such as urethane, PVC (polyvinyl chloride), fluoropolymer, fluoroelastomer or the like may be disposed over the braided cord. As an alternative to wire or cord, flat metal strips may be helically wrapped around extruded tube 104 to provide torsional stiffening. Preferably, if a torsional-stiffening layer is included, it will extend from the control assembly to the proximal edge of the sample storage area, so as not to occlude the viewing of tissue samples within the lumen of flexible body 52.

Figure 22:
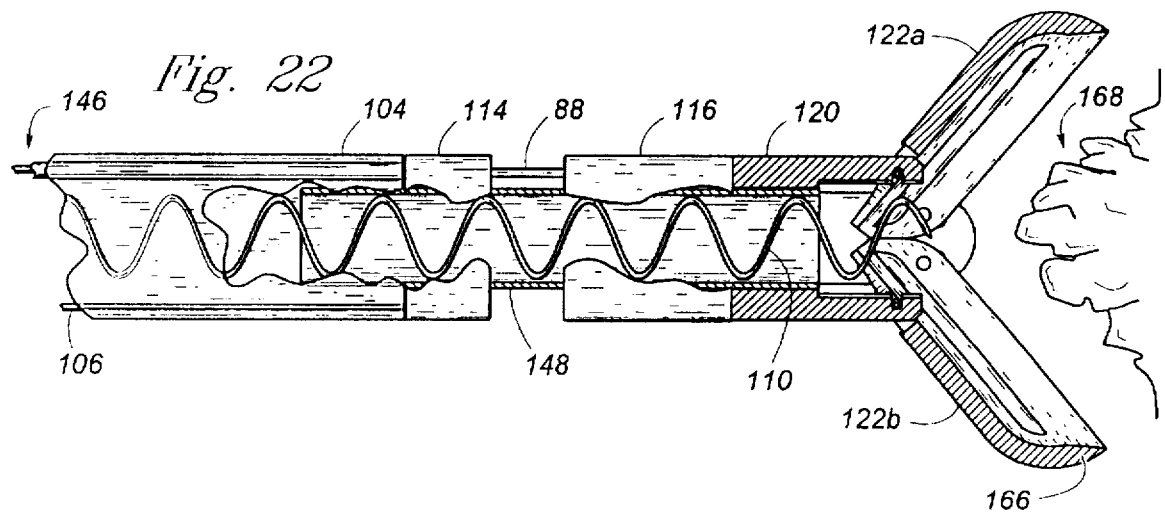
FIG. 22 is an enlarged view of the distal region of the preferred embodiment, with portions broken away to reveal underlying structures, and showing the jaws fully open, poised to capture a tissue sample.
Figure 23:
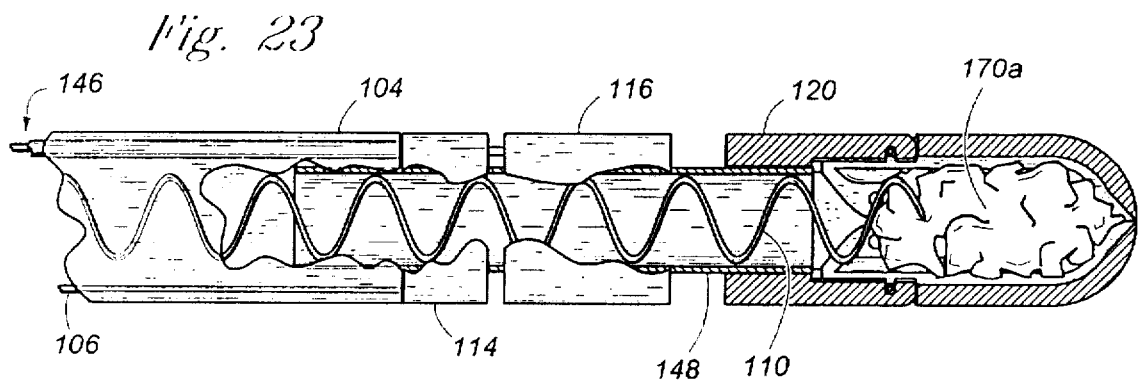
FIG. 23 is an enlarged view of the distal region of the preferred embodiment, with portions broken away to reveal underlying structures, and showing the jaws closed around a tissue sample.
Figure 24:
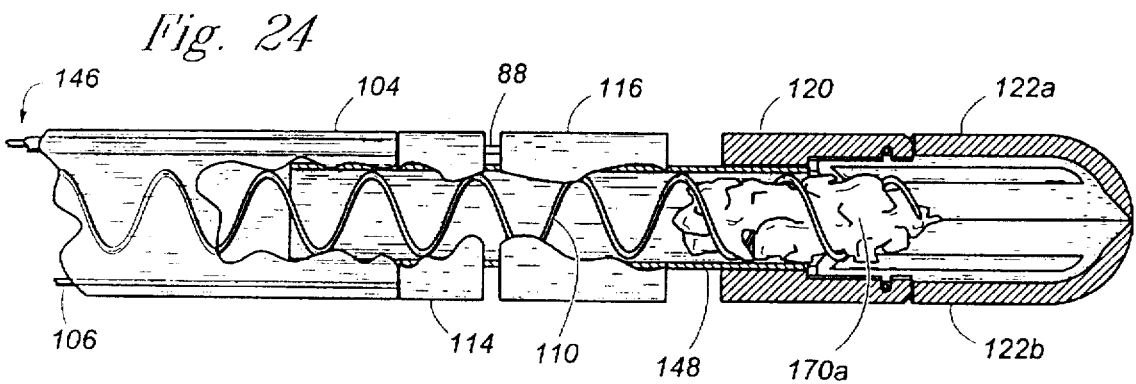
FIG. 24 is an enlarged view of the distal region of the preferred embodiment, with portions broken away to reveal underlying structures, and showing the helical coil engaging a captured tissue sample.
Figure 25:
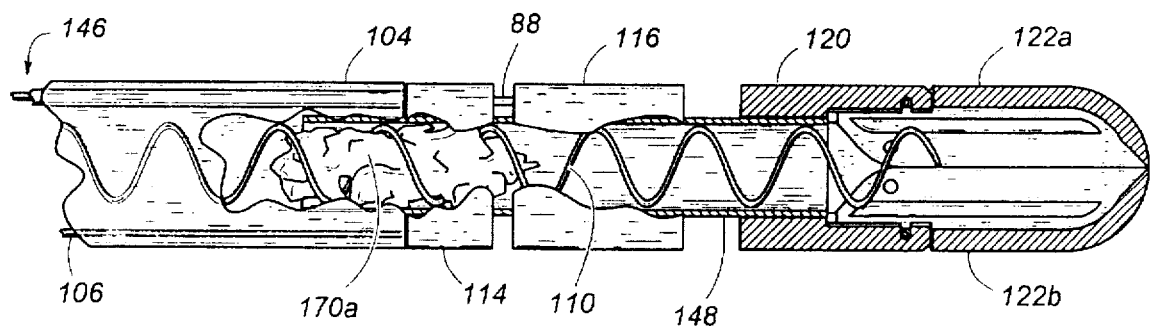
FIG. 25 is an enlarged view of the distal region of the preferred embodiment, with portions broken away to reveal underlying structures, and showing the helical coil drawing a captured tissue sample into the lumen of the flexible body.

FIG. 22 shows an enlarged view of the distal region of the preferred embodiment. Control wire 88 has been pushed distally, forcing sliding collar 116 to slide distally and causing jaws 122a and 122b to open. In the illustration, the jaws have been positioned adjacent to tissue mass 168. In FIG. 23, jaws 122a and 122b have been closed by pulling on control wire 88, thus capturing tissue sample 170a within the jaws. The distal tip of helical coil 110 is in contact with the proximal portion of tissue sample 170a. In FIG. 24, drive shaft 78 (not shown) is rotated to turn helical coil 110. As helical coil 110 turns, the tip of the coil engages tissue sample 170a. Fins 138 (Refer to FIG. 18) on the inner surfaces of the jaws prevent tissue sample 170a from rotating. As a result, continued turning of helical coil 110 draws tissue sample 170a in a proximal direction. As the tissue sample is drawn into connecting tube 148, the longitudinal ribs disposed along the inner surface of connecting tube 148 continue to prevent rotation of tissue sample 170a. As shown in FIG. 25, tissue sample 170a eventually is pulled through connecting tube 148 to the central lumen of extruded tube 104. At this point, if the device is being used with an endoscope, the clinician may choose to deflect the distal region in order to observe advancement of tissue sample 170a into sample collection region 56.

Figure 26:
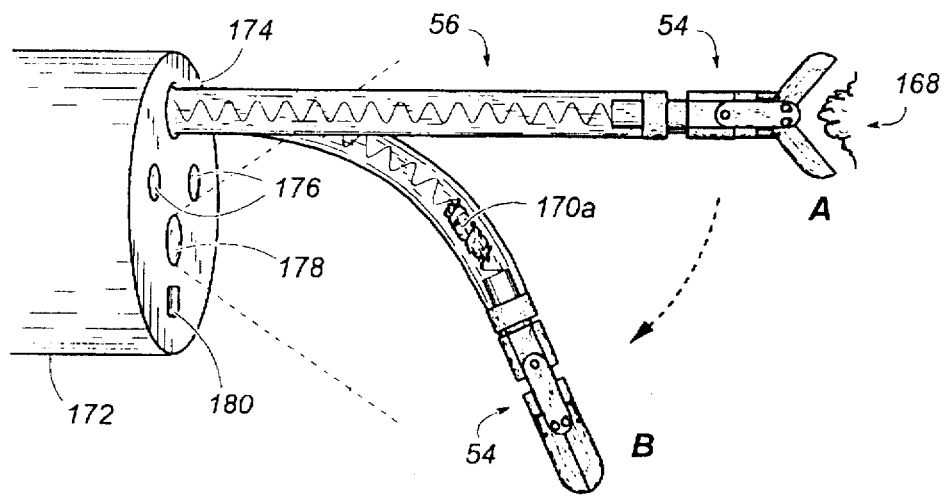
FIG. 26 is a perspective view of the preferred embodiment shown extending out of the distal face of a flexible endoscope; in position "A" the forceps are shown poised to capture a tissue sample, while in position "B" they are shown in a deflected posture with a sample drawn into the lumen of the flexible body.

In FIG. 26, the preferred embodiment is shown extending out of the distal face of endoscope 172. On the face of endoscope 172 are disposed illuminating windows 176, imaging lens 178, lens rinse nozzle 180 and the distal opening of the forceps channel 174. The dashed lines angling from imaging lens 78 indicate a typical field of view for an endoscope. The distal region of the preferred embodiment is shown in a first undeflected position "A," and a second deflected position "B." In position A, the device is poised to bite tissue mass 168. In position B, tissue sample 170a has been engulfed and drawn into sample collection region 56. As can be seen, the deflection capability greatly enhances the clinician's ability to observe the movement of tissue sample 170a, not only because the long axis of collection region 56 is now across the field of view, but also because it is now within the region illuminated by illuminating windows 176.

Figure 27:
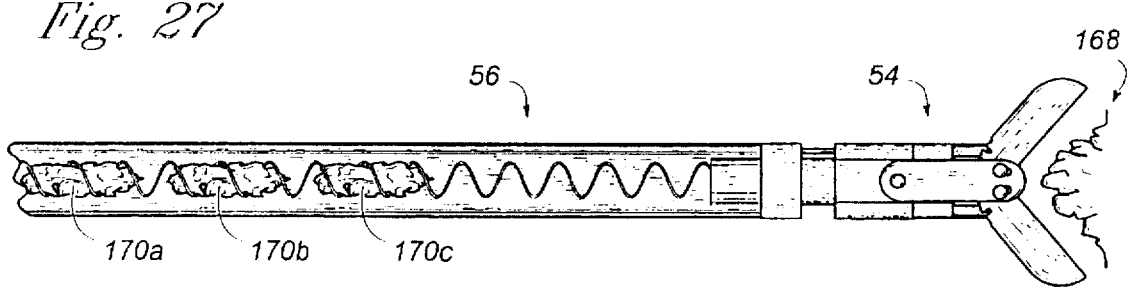
FIG. 27 is an enlarged side view of the distal region of the preferred embodiment, shown with three tissue samples in the lumen of the flexible body and the jaws poised to capture another sample.

FIG. 27 shows the distal region of the preferred embodiment poised to excise a sample from tissue mass 168 after three tissue samples, 170a through 170c, have already been drawn into sample collection region 56. The spacing between consecutive samples in the collection region can be controlled by the clinician. As can be seen in the figure, the first three samples are spaced fairly closely together, while a larger space has been left between tissue sample 170c and jaw assembly 54. The larger space is created simply by turning helical coil 110 to move the captured samples farther proximally within the lumen. In this manner, the clinician can keep track of clusters of samples taken from specific regions of a patient simply by leaving a larger space between sample groups.

Figure 28:
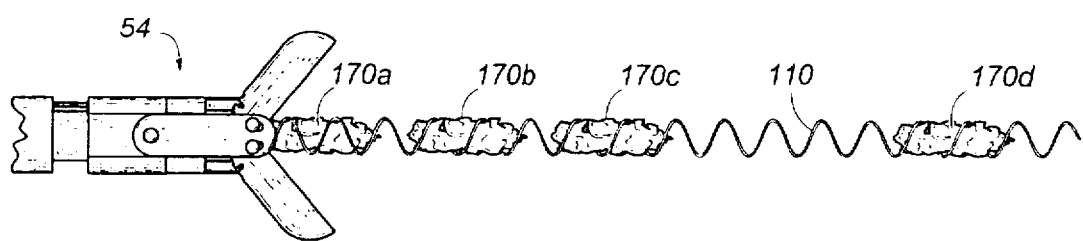
FIG. 28 shows the jaw assembly of the embodiment illustrated in FIG. 27, with the helical coil pushed out through the jaws to allow removal of the captured samples.

In FIG. 28, helical coil 110 has been pushed distally through jaw assembly 54 in order to allow removal of the tissue samples from the coil. The distal movement of helical coil 110 is accomplished by inserting a tool into access hole 182 of control assembly 50, as best seen in FIG. 3, and pushing on drive shaft 78. As shown in FIG. 28, helical coil 110 does not pierce the tissue samples, but rather wraps around the outside of them. Thus, it is easy to remove the samples from the coil either by shaking the coil in a fluid-filled sample container or by plucking the samples off the coil with tweezers.

From the foregoing, it will be appreciated that the present invention provides a biopsy forceps device with improvements in accordance with the above-described objects. While particular embodiments of the invention are described herein, it is not intended that the invention be limited exactly thereto, as it is intended that the invention be as broad in scope as the art will permit. Thus, while the embodiments presented describe specific combinations of actuating means, intake means, deflection means, control means and the like, it will be appreciated that the presentation is not intended to be exhaustive. Numerous alternate combinations are readily conceivable to those skilled in the art. For example, the control assembly may be re-configured for single-handed operation, if desired. It will also be appreciated that the invention disclosed herein may represent a portion of a more complicated device, rather than a stand-alone instrument. In such applications, supplemental features may be added to the invention disclosed such as additional lumina, more versatile control assemblies, optical waveguides, fluid conduits and the like. Further, it will appreciated that multiple deflection means may be incorporated into the invention to impart a multi-axis deflection capability to the device. Also, parts depicted as being separate may be integrated into unitary structures without departing from the scope of the invention. In addition, while the particular embodiments depicted herein show the intake means in the form of a helical coil, numerous other mechanisms are conceivable to accomplish the same function. Moreover, while various materials are described as being preferred for various parts, it will be appreciated that other appropriate materials may be utilized. Therefore, it will be apparent to those skilled in the art that other changes and modifications may be made to the invention as described in the specification without departing from the spirit and scope of the invention as so claimed.

Although this invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

We claim:

1. In an actuating assembly for obtaining a plurality of tissue samples from a wall defining a cavity in a patient, for retaining the tissue samples, a flexible tube having a lumen extending through the tube and defining a long axis, the flexible tube being constructed to be variably positioned in the cavity in the patient, an effector assembly coupled to the tube and having first and second operative relationships, the effector assembly being operative in each of successive first relationships to accept portions of tissue from the wall of the cavity in the patient and being operative in each of the second relationships to remove and retain each of the tissue samples in the plurality, and means within the lumen for advancing each of the removed tissue samples in the plurality through the lumen in the flexible tube in accordance with the removal of the successive ones of the tissue samples from the cavity in the patient.

2. In an actuating assembly as set forth in claim 1, the advancing means being operative without requiring a differential atmospheric pressure between the first and second ends of the flexible tube.

3. In an actuating assembly as set forth in claim 1, means for removing the tissue samples from the lumen in the flexible tube after the removal of the flexible tube from the cavity in the patient.

4. In an actuating assembly as set forth in claim 1, the effector assembly including a rotatable member for holding the tissue samples in the lumen in the tube and further including means associated with the rotatable member for translating the rotation of the rotatable member into a movement of the tissue samples in the direction of the long axis of the flexible tube.

5. In an actuating assembly for obtaining a plurality of tissue samples from a wall defining a cavity in a patient, for retaining the tissue samples, a flexible tube having a lumen extending through the tube and defining a long axis, the flexible tube being constructed to be variably positioned in the cavity in the patient, an effector assembly coupled to the tube and having first and second operative relationships, the effector assembly being operative in each of successive first relationships to accept portions of tissue from the wall of the cavity in the patient and being operative in each of the second relationships to remove and retain each of the tissue samples in the plurality, the effector assembly including a pair of jaws movable between an open disposition relative to each other in the first relationship and a closed disposition relative to each other in the second relationship, the jaws being disposed relative to each other to define a cavity which communicates with the lumen in the flexible tube for obtaining an advance of the tissue samples from such cavity into the lumen in the flexible tube, and means for advancing each of the removed tissue samples in the plurality through the lumen in the flexible tube in accordance with the removal of the successive ones of the tissue samples from the cavity in the patient.

6. In an actuating assembly as set forth in claim 5, the effector assembly including a pair of pivotable jaws having open and closed positions relative to each other with the open position of the jaws providing the first relationship and with the closed position of the jaws providing the second relationship, the effector assembly including means responsive to the movements of a control wire for pivoting the pair of jaws between the open and closed positions, the jaws being disposed relative to each other and being constructed to define a cavity which communicates with the lumen in the flexible tube for obtaining an advance of the tissue samples from such cavity into the lumen in the flexible tube.

7. In an actuating assembly as set forth in claim 6, the advancing means being operative without requiring a differential atmospheric pressure between the first and second ends of the flexible tube, means for removing the tissue samples from the lumen in the tube after the removal of the tube from the cavity in the patient, the effector assembly including a rotatable member for holding the tissue samples in the lumen in the flexible tube and further including means associated with the rotatable member for translating the rotation of the rotatable member into a movement of the tissue samples in the lumen in the flexible tube in the direction of the long axis of the tube.

8. In an actuating assembly for obtaining a plurality of tissue samples from a wall defining a cavity in a patient and for retaining the tissue samples, a flexible tube having a lumen extending through the tube, the flexible tube being constructed to be variably positioned in the cavity in the patient, an effector assembly communicating with the lumen in the tube, the effector assembly having first and second operative relationships and operative in the first relationship to accept tissue from the wall of the cavity in the patient and operative in the second relationship to remove and retain a tissue sample, first means disposed in the tube for providing a controlled operation of the effector assembly in the first and second relationships, and second means disposed in the tube for providing a transfer of the tissue samples into the tube after the removal of the tissue samples from the wall in the cavity.

9. In an actuating assembly as set forth in claim 8, the second means being operative to transfer the tissue samples into the flexible tube in the same order as the tissue samples are produced by successive operations of the effector assembly between first and second operative relationships.

10. In an actuating assembly as set forth in claim 8, the second means including a coil disposed in the tube for retaining the tissue samples in the flexible tube and including means for rotating the coil and including means associated with the coil for converting the rotations of the coil into movements of the tissue samples in the flexible tube in a direction corresponding at progressive positions to the disposition of the flexible tube in the cavity in the patient.

11. In an actuating assembly as set forth in claim 8, retaining means disposed in the flexible tube for the tissue samples provided by the effector assembly, third means for producing a rotation of the retaining means, and fourth means for converting the rotational movement of the retaining means into a movement of the tissue samples into the flexible tube with minimal rotation of the tissue samples.

12. In an actuating assembly as set forth in claim 8, third means movable into the actuating assembly for operating upon the second means to obtain a transfer of the tissue samples from the flexible tube.

13. In an actuating assembly as set forth in claim 8, the effector assembly including a pair of pivotable jaws having open and closed positions relative to each other with the open position of the jaws providing the first relationship and with the closed position of the jaws providing the second relationship, the effector assembly including means operatively coupled to the effector assembly for pivoting the pair of jaws between the open and closed positions, the jaws being disposed relative to each other and being constructed to define an opening which communicates with the lumen in the tube for obtaining an advance of the tissue samples from such opening into the lumen.

14. In an actuating assembly as set forth in claim 13, retaining means disposed in the flexible tube for the tissue samples provided by the effector assembly, third means for producing a rotation of the retaining means, and fourth means for converting the rotational movement of the retaining means into a movement of the tissue into the flexible tube with minimal rotation of the tissue samples, and fifth means movable into the actuating assembly for operating upon the second means to obtain a transfer of the tissue samples from the flexible tube.

15. In an actuating assembly for obtaining a plurality of tissue samples from a wall defining a cavity in a patient and for retaining the tissue samples, a flexible tube having a lumen extending through the tube and defining a long axis, the flexible tube being constructed to be variably positioned in the cavity in the patient, an effector assembly having first and second operative relationships and operative in the first relationship to accept tissue from the wall of the cavity and operative in the second relationship to remove and retain a tissue sample, the effector assembly defining a passage communicating with the lumen in the flexible tube, first means disposed along the long axis of the tube and operatively coupled to the effector assembly for providing a controlled operation of the effector assembly in individual ones of the first and second relationships, and second means disposed in the lumen in the flexible tube for providing for the transfer into the lumen in the flexible tube of the tissue samples removed from the wall of the cavity by the effector assembly and for providing for a progressive displacement of such tissue samples from the effector assembly into the lumen in the flexible tube to provide for the reception of subsequent ones of the tissue samples in the flexible tube.

16. In an actuating assembly as set forth in claim 15, the second means being constructed to envelope the tissue samples transferred into the lumen in the flexible tube and to maintain this enveloping relationship during the progressive displacement of such tissue samples into the lumen in the tube.

17. In an actuating assembly as set forth in claim 16, the second means including a coil disposed in the lumen in the flexible tube and enveloping the tissue samples in the lumen.

18. In an actuating assembly as set forth in claim 15, means for providing for a removal of the tissue samples from the lumen in the flexible tube in an order opposite to the order in which the tissue samples have been transferred into the lumen in the flexible tube.

19. In an actuating assembly as set forth in claim 16, the second means including a coil disposed in the lumen in the tube and enveloping the tissue samples in the lumen, and third means for providing for a removal of the tissue samples from the lumen in the flexible tube in an order opposite to the order in which the tissue samples have been transferred into the lumen in the flexible tube.

20. In an actuating assembly for obtaining a plurality of tissue samples from a wall defining a cavity in a patient, a flexible tube having a lumen extending through the tube, the flexible tube being constructed to be variably positioned in the cavity in the patient, an effector assembly having first and second operative relationships and operative in the first relationship to accept tissue from the wall of the cavity and operative in the second relationship to remove and retain a tissue sample from the wall of the cavity, the effector assembly defining a passage communicating with the lumen in the flexible tube, first means in the effector assembly for retaining in the lumen in the flexible tube the tissue samples removed by the effector assembly from the wall of the cavity, and second means for removing the tissue samples from the lumen in the tube in an order inverse to the order in which such tissue samples are retained in the tube.

21. In an actuating assembly as set forth in claim 20, the effector assembly being operative in the first relationship during the removal of the tissue samples from the lumen in the flexible tube.

22. In an actuating assembly as set forth in claim 20, the first means including a helical coil extending through the lumen in the flexible tube.

23. In an actuating assembly as set forth in claim 21, the effector assembly being operative in the first relationship during the removal of the tissue samples from the lumen in the flexible tube, the first means including a member extending through the flexible tube for enveloping the tissue samples disposed in spaced relationship in the lumen in the flexible tube, and the second means being operative to move the first means through the lumen in the flexible tube with the effector assembly in the first operative relationship and through the effector assembly to the atmosphere.

24. In an actuating assembly as set forth in claim 23, the effector assembly including a pair of jaws having open and closed positions relative to each other and the jaws being open in the first operative relationship of the effector assembly and being closed the second operative relationship of the effector assembly, and the second means being operative to move the retaining means through the lumen in the flexible tube and through the effector assembly with the jaws in the open position to expose the tissue samples for removal from the first means.

25. In an actuating assembly as set forth in claim 24, the first means including a helical coil extending through the lumen in the flexible tube, the effector assembly being operative in the first relationship during the removal of the tissue samples from the lumen in the flexible tube.

26. In an actuating assembly for obtaining a plurality of tissue samples from a wall defining a cavity in a patient and for retaining the tissue samples, a flexible tube having a lumen extending through the tube, the flexible tube being constructed to be variably positioned in the cavity in the patient, an effector assembly having first and second operative relationships and operative in the first relationship to accept tissue from the wall defining the cavity in the patient and operative in the second relationship to provide for a removal and retention of tissue samples in the effector assembly and in the lumen in the flexible tube, first means in the flexible tube for advancing the tissue samples from the effector assembly into the lumen in the flexible tube, and second means in the flexible tube for providing a controlled bending of the flexible tube.

27. In an actuating assembly as set forth in claim 26, the flexible tube being transparent to provide for a viewing of the tissue samples in the flexible tube.

28. In an actuating assembly as set forth in claim 27, means for illuminating the flexible tube to facilitate the viewing of the tissue samples in the flexible tube.

29. In an actuating assembly as set forth in claim 26, third means associated with the first means for providing for a removal of the tissue samples from the lumen in the flexible tube after the transfer of the tissue samples into the lumen in the flexible tube.

30. In an actuating assembly as set forth in claim 26, the first means including third means for enveloping the tissue samples removed from the wall of the cavity in the patient and fourth means for operating upon the third means to transfer the tissue samples along the third means into the lumen in the flexible tube.

31. In an actuator assembly as set forth in claim 26, the effector assembly having a pair of jaws pivotable between open and closed positions and providing the first relationship in the open position and the second relationship in the closed position, and means for providing a controlled opening and closing of the jaws in the effector assembly.

32. In an actuator assembly as set forth in claim 31, the flexible tube being transparent to provide for a viewing of the tissue samples in the flexible tube, means associated with the first means for providing for a removal of the tissue samples from the lumen in the flexible tube after the transfer of the tissue samples into the lumen in the flexible tube, the first means including third means for enveloping the tissue samples removed from the wall of the cavity in the patient and fourth means for operating upon the third means to transfer the tissue samples along the third means into the lumen in the flexible tube.

33. In an actuating assembly as set forth in claim 29, the third means being operative to provide for a removal of the tissue samples from the lumen in the flexible tube with the effector assembly in the first relationship.

34. In an actuating assembly for obtaining a tissue sample from a wall defining a cavity in a patient and for retaining the tissue sample, a flexible tube having a lumen extending through the flexible tube and defining a long axis, the flexible tube being constructed to be variably positioned in the cavity in the patient, an effector assembly having first and second operative relationships and operative in the first relationship to accept tissue from the wall of the cavity and operative in the second relationship to remove and retain a tissue sample from the wall of the cavity, first means disposed along the long axis of the flexible tube and operatively coupled to the effector assembly in the first and second relationships, second means disposed externally of the flexible tube and operatively coupled to the first means for obtaining the operation by the first means of the effector assembly in the first and second relationships, third means for retaining the tissue sample in the lumen in the flexible tube, and fourth means disposed externally of the flexible tube and operative upon the third means for moving the third means through the flexible tube and through the effector assembly in the first operative relationship of the effector assembly to expose the tissue to the atmosphere.

35. In an actuating assembly as set forth in claim 34, the third means including a coil enveloping the tissue sample in the lumen in the flexible tube.

36. In an actuating assembly as set forth in claim 34, the second means being movable in the direction of the long axis to provide a movement of the first means in the direction of the long axis, the effector assembly being responsive to the direction of the movement of the first means in the flexible tube for providing an operation of the effector assembly in an individual one of the first and second relationships.

37. In an actuating assembly as set forth in claim 34, the first means being movable along the flexible tube in the direction of the long axis to operate the effector assembly in the first and second relationships in accordance with such movements, the fourth means being operable to move the third means in the direction of the long axis for a movement of the third means through the flexible tube and through the effector assembly in the first operative relationship of the effector assembly to a position exposing the tissue sample to the atmosphere.

38. In an actuating assembly as set forth in claim 34, the effector assembly including a pair of jaws pivotable relative to each other between an open position and a closed position, the open position of the jaws providing an operation of the effector assembly in the first relationship and the closed position of the jaws providing an operation of the effector assembly in the second relationship, and the effector assembly including means responsive to the operation of the second means for obtaining a pivotal movement by the first means of the jaws between the closed and open positions.

39. In an actuating assembly as set forth in claim 38, the third means including a coil enveloping the tissue sample in the lumen in the flexible tube, the first means being movable in the direction of the long axis to operate the effector assembly in the first and second relationships in accordance with such movements, the fourth means being operable to move the third means through the flexible tube and through the effector assembly to a position exposing the tissue sample to the atmosphere with the effector assembly in the first operative relationship.

40. In an actuating assembly for obtaining a tissue sample from a wall defining a cavity in a patient and for retaining the tissue sample, a flexible tube having a lumen extending through the flexible tube and defining a long axis the flexible tube being constructed to be variably positioned in the cavity in the patient, an effector assembly having first and second operative relationships and operative in the first relationship to accept tissue from the wall of the cavity and operative in the second relationship to remove and retain a tissue sample from the wall of the cavity, first means disposed a long the long axis of the flexible tube and operatively coupled to the effector assembly for providing an operation of the effector assembly in the first and second relationships, second means disposed externally of the flexible tube and operatively coupled to the first means for obtaining the operation by the first means of the effector assembly in the first and second relationships, third means disposed in the lumen in the flexible tube for operating upon the tissue sample in the effector assembly to obtain a transfer of the tissue sample from the effector assembly into the lumen in the flexible tube, and fourth means disposed externally of the flexible tube and operatively coupled to the third means for obtaining a transfer by the third means of the tissue sample from the effector assembly into the lumen in the flexible tube.

41. In an actuating assembly as set forth in claim 40, the third means being constructed to be rotary and enveloping the tissue sample in the lumen in the flexible tube, the fourth means being operative to rotate the third means to obtain a transfer of the tissue sample by the third means into the lumen in the flexible tube, and fifth means associated with the third means for translating the rotary movement of the third means into a movement of the tissue sample along the long axis into the lumen in the flexible tube.

42. In an actuating assembly as set forth in claim 41, the third means including a coil enveloping the tissue sample in the lumen in the flexible tube, and the fifth means including ribs disposed relative to coil and to the tissue sample enveloped by the coil for translating the rotary movement of the third means into the directional movement of the tissue sample into the lumen in the flexible tube.

43. In an actuating assembly as set forth in claim 40, the effector assembly including a pair of pivotable jaws having open and closed positions relative to each other and providing the first operative relationship in the open position and providing the second operative relationship in the closed position, and the first means including a control wire and second means associated with the control wire for pivoting the jaws between the open and closed positions.

44. In an actuating assembly as set forth in claim 43, the second means being movable in the direction of the long axis to provide a movement of the control wire in the in the direction of the long axis.

45. In an actuating assembly as set forth in claim 40, the effector assembly including a pair of jaws pivotable relative to each other between an open position and a closed position, the open position of the jaws providing an operation of the effector assembly in the first relationship and the closed position of the jaws providing an operation of the effector assembly in the second relationship, and the effector assembly including means responsive to the operation of the second means for obtaining a pivotal movement by the first means of the jaws between the closed and open positions.

46. In an actuating assembly as set forth in claim 45, the third means being constructed to be rotary and enveloping the tissue sample in the lumen in the flexible tube, the fourth means being operative to rotate the third means to obtain a transfer of the tissue sample by the third means into the lumen in the flexible tube, and fifth means associated with the third means for translating the rotary movement of the third means into a directional movement of the tissue sample along the long axis into the lumen in the flexible tube, the third means including a coil enveloping the tissue sample in the lumen in the flexible tube, and the fifth means including ribs disposed relative to coil and to the tissue sample enveloped by the coil for translating the rotary movement of the third means into the directional movement of the tissue sample into the lumen in the flexible tube, the effector assembly including a pair of pivotable jaws having open and closed positions relative to each other and providing the first operative relationship in the open position and providing the second operative relationship in the closed position, and the first means including a control wire and second means associated with the control wire for pivoting the jaws between the open and closed positions, and the second means being movable in the direction of the long axis to provide a movement of the control wire in the direction of the long axis.

47. In an actuating assembly for obtaining a tissue sample from a wall defining a cavity in a patient and for retaining the tissue sample, an effector assembly having first and second operative relationships and operative in the first relationship to accept tissue from the wall of the cavity and operative in the second relationship to remove and retain a tissue sample from the wall of the cavity, first means disposed along the tube and operatively coupled to the effector assembly for providing an operation of the effector assembly in the first and second relationships, second means disposed externally of the tube and operatively coupled to the first means for obtaining the operation by the first means of the effector assembly in the first and second relationships, third means disposed in the lumen in the flexible tube for operating upon the tissue sample in the effector assembly to obtain a transfer of the tissue sample from the effector assembly into the lumen in the flexible tube, fourth means disposed externally of the flexible tube and operatively coupled to the third means for obtaining a transfer by the third means of the tissue sample from the effector assembly into the lumen in the flexible tube, and fifth means operatively coupled to the third means for obtaining a transfer of the third means from the lumen in the flexible tube to the atmosphere.

48. In an actuating assembly as set forth in claim 47, the third means including sixth means disposed in the lumen in the flexible tube for enveloping the tissue sample to obtain the transfer of the tissue sample from the effector assembly into the lumen in the flexible tube, the effector assembly being constructed to provide an aperture communicating with the lumen in the flexible tube for providing for the passage of the tissue sample through the aperture into the lumen in the flexible tube in accordance with the operation of the fourth means.

49. In an actuating assembly as set forth in claim 48, the fifth means being coupled to the sixth means for obtaining the transfer of the tissue sample from the lumen in the tube to the atmosphere with the effector assembly in the first relationship.

50. In an actuating assembly as set forth in claim 47, the flexible tube having a long axis, the fourth means being rotatable and the third means being operative to translate the rotary motion of the fourth means into a motion of the tissue sample in a first direction along the long axis of the tube, and the fifth means being operative to produce a motion of the third means along the long axis of the tube in a second direction opposite to the first direction.

51. In an actuating assembly as set forth in claim 47, the third means including sixth means disposed in the lumen in the tube for enveloping the tissue sample to obtain the transfer of the tissue sample from the effector assembly into the lumen in the flexible tube, the effector assembly being constructed to provide an aperture communicating with the lumen in the flexible tube for providing for the passage of the tissue sample through the aperture into the lumen in the flexible tube in accordance with the operation of the fourth means, the fifth means being coupled to the sixth means for obtaining the transfer of the tissue sample from the lumen in the flexible tube to the atmosphere with the effector assembly in the first relationship.

52. In an actuating assembly as set forth in claim 51, the effector assembly including a pair of jaws pivotable relative to each other between the first and second positions and providing the first relationship in the open position and providing the second relationship in the closed position, the first means being responsive to the operation of the second means for pivoting the jaws on a controlled basis between the open and closed positions.

53. In an actuating assembly for obtaining a tissue sample from a wall defining a cavity in a patient and for retaining the tissue sample, a flexible tube having a lumen extending through the flexible tube, the flexible tube being constructed to be variably positioned in the cavity in the patient, an effector assembly having first and second operative relationships and operative in the first relationship to accept tissue from the wall of the cavity and operative in the second relationship to remove and retain a tissue sample in the effector assembly, first means operatively coupled to the effector assembly for obtaining a controlled operation of the effector assembly in the first and second relationships, second means disposed in the lumen for obtaining a transfer of the removed tissue sample into the lumen in the flexible tube, and third means for providing a transfer of the removed tissue from the lumen in the flexible tube to the atmosphere with the effector assembly in the first relationship.

54. In an actuating assembly as set forth in claim 53, the second means including fourth means disposed in the lumen for enveloping the tissue sample and for displacing the tissue sample into the lumen, the third means providing for the movement of the fourth means to the atmosphere through the lumen in the flexible tube and through the effector assembly with the effector assembly in the first relationship.

55. In an actuating assembly as set forth in claim 53, the lumen in the flexible tube having a long axis, the second means including a helical coil disposed in the lumen for enveloping the tissue sample and including fourth means for providing a rotary movement of the helical coil and including fifth means for translating such rotary movement into a movement of the tissue sample in the helical coil along the long axis of the lumen in the flexible tube, the third means providing for the movement of the helical coil to the atmosphere through the lumen in the flexible tube and through the effector assembly with the effector assembly in the first relationship.

56. In an actuating assembly as set forth in claim 53, the effector assembly including a pair of jaws pivotable relative to each other between an open position and closed position, the effector assembly providing the first relationship in the open position and providing the second relationship in the closed position, the first means being operative to provide a pivotable movement of the jaws to the open position at first particular times and to provide a pivotable movement of the jaws to the closed position at second times different from the first particular times.

57. In an actuating assembly as set forth in claim 56, the second means including fourth means disposed in the lumen for enveloping the tissue sample and for displacing the tissue sample into the lumen, the third means providing for the movement of the fourth means to the atmosphere through the lumen in the tube and through the effector assembly with the effector assembly in the first relationship.

58. In an actuating assembly as set forth in claim 56, the lumen in the tube having a long axis, the second means including a helical coil disposed in the lumen for enveloping the tissue sample and including fourth means for providing a rotary movement of the helical coil and including fifth means for translating such rotary movement into a directional movement of the tissue sample in along the long axis of the lumen in the tube, the third means providing for the movement of the helical coil to the atmosphere through the lumen in the tube and through the effector assembly with the effector assembly in the first relationship.

59. In an actuating assembly for obtaining a tissue sample from a wall defining a cavity in a patient and for retaining the tissue sample, a flexible tube having a lumen extending through the flexible tube, the flexible tube being constructed to be variably positioned in the cavity in the patient, an effector assembly having first and second operative relationships and operative in the first relationship to accept tissue from the wall of the cavity and operative in the second relationship to remove and retain a tissue sample in the effector assembly, first means operatively coupled to the effector assembly for providing a controlled operation of the effector assembly in the first and second relationships, second means for obtaining a transfer of the removed tissue sample into the lumen in the flexible tube, and third means for providing a controlled bending of the flexible tube to facilitate the viewing of the tissue sample in the flexible tube.

60. In an actuating assembly as set forth in claim 59, the flexible tube being transparent at the positions of the bending of the flexible tube to facilitate the viewing of the tissue sample in the flexible tube.

61. In an actuating system as set forth in claim 59, the lumen in the tube having a long axis, the second means including fourth means disposed in the lumen for enveloping the tissue sample and for displacing the tissue sample into the lumen and including fifth means for providing a rotary movement of the fourth means and including sixth means for translating such rotary movement into a movement of the tissue sample along the long axis of the lumen in the tube.

62. In an actuating assembly as set forth in claim 59, the lumen in the tube having a long axis, the third means including fourth means movable along the long axis of the tube for producing a tensile force on the tube in the direction of the long axis and including fifth means disposed in the tube at a particular side of the tube for restricting the stretching of the tube at such side to obtain a bending of the tube in a direction toward the particular side.

63. In an actuating assembly as set forth in claim 59, the effector assembly including a pair of jaws pivotable relative to each other between open and closed positions, the jaws providing the first relationship in the open position and providing the second relationship in the closed position, the first means being operative to pivot the jaws to the open position at first particular times and to pivot the jaws to the closed position at second particular times different from the first particular times.

64. In an actuating assembly as set forth in claim 61, the third means including sixth means movable along the long axis of the tube for producing a tensile force on the tube in the direction of the long axis and including seventh means disposed in the tube at a particular side of the tube for restricting the stretching of the tube at such side to obtain a bending of the tube in a direction toward the particular side, the effector assembly including a pair of jaws pivotable relative to each other between closed and open positions, the jaws providing the first relationship in the open position and providing the second relationship in the closed position, the first means being operative to pivot the jaws to the open position at first particular times and to pivot the jaws to the closed position at second particular times different from the first particular times.

65. In an actuating assembly for obtaining a tissue sample from a wall defining a cavity in a patient and for retaining the tissue sample, a flexible tube having a lumen extending through the flexible tube, the flexible tube being constructed to be variably positioned in the cavity in the patient, an effector assembly having first and second operative relationships and operative in the first relationship to accept tissue from the wall of the cavity and operative in the second relationship to remove and retain a tissue sample in the effector assembly, first means disposed in the tube and operatively coupled to the effector assembly for obtaining a controlled operation of the effector assembly in the first and second relationships, second means disposed externally of the tube and operatively coupled to the first means for obtaining the operation by the first means of the effector assembly in the first and second operative relationships, third means disposed in the lumen in the flexible tube for operating upon the tissue sample in the effector assembly to obtain a transfer of the tissue sample from the effector assembly into the lumen in the flexible tube, fourth means disposed externally of the flexible tube and operatively coupled to the third means for obtaining a transfer by the third means of the tissue sample from the effector assembly into the lumen in the flexible tube, fifth means for providing a controlled bending of the flexible tube, and sixth means disposed externally of the flexible tube and operatively coupled to the fifth means for obtaining a controlled bending of the flexible tube by the fifth means.

66. In an actuating assembly as set forth in claim 65, the flexible tube being transparent in positions between the controlled bending of the flexible tube and the effector assembly to provide for the visual viewing of the tissue sample in the flexible tube.

67. In an actuating assembly as set forth in claim 65, the lumen extending in the flexible tube in a long axis, the third means being constructed to be rotary and enveloping the tissue sample in the lumen in the flexible tube, the fourth means being operative to rotate the third means to obtain a transfer of the tissue sample by the third means into the lumen in the flexible tube, and seventh means associated with the third means for translating the rotary movement of the third means into a movement of the tissue sample along the long axis into the lumen in the tube.

68. In an actuating assembly as set forth in claim 65, the lumen in the tube having a long axis, the fifth means including seventh means movable along the long axis of the flexible tube for producing a tensile force on the flexible tube in the direction of the long axis and including eighth means disposed in the flexible tube at a particular side of the tube for restricting the stretching of the flexible tube at such side to obtain a bending of the tube in a direction toward the particular side.

69. In an actuating assembly as set forth in claim 68, the sixth means being constructed to be rotary, and the fifth means including ninth means responsive to the rotary movement of the sixth means for translating such rotary movement into the production by the fifth means of the tensile force on the tube in the direction of the long axis.

70. In an actuating assembly as set forth in claim 65, the effector assembly including a pair of jaws providing the first relationship in the open position and providing the second relationship in the closed position, and the first means being operatively coupled to the jaws to pivot the jaws between the open and closed positions.

71. In an actuating assembly as set forth in claim 65, the lumen in the tube having a long axis, the fifth means including seventh means movable along the long axis of the tube for producing a tensile force on the flexible tube in the direction of the long axis and including eighth means disposed in the flexible tube at a particular side of the flexible tube for restricting the stretching of the flexible tube at such side to obtain bending of the tube in a direction toward the particular side, the sixth means being constructed to be rotary, and the fifth means including ninth means responsive to the rotary movement of the sixth means for translating such rotary movement into the production by the fifth means of the tensile force on the flexible tube in the direction of the long axis.

72. In an actuating assembly for obtaining a tissue sample from a wall defining a cavity in a patient and for retaining the tissue sample, a flexible tube having a lumen extending through the flexible tube, the flexible tube being constructed to be variably positioned in the cavity in the patient, an effector assembly having first and second operative relationships and operative in the first relationship to accept tissue from the wall of the cavity and operative in the second relationship to remove and retain a tissue sample in the effector assembly, first means operatively coupled to the effector assembly for providing a controlled operation of the effector assembly in the first and second relationships, second means disposed in the lumen for obtaining a transfer of the removed tissue sample into the lumen in the flexible tube, and third means for obtaining a transfer of the tissue sample in the lumen in the flexible tube through the effector assembly for examination of the tissue sample.

73. In an actuating assembly as set forth in claim 72, the effector assembly being operative in the first relationship during the transfer of the tissue sample through the effector assembly for examination of the tissue sample.

74. In an actuating assembly as set forth in claim 72, the second means including fourth means disposed in the lumen in the tube for retaining the tissue sample, the third means being operative to move the fourth means through the lumen in the tube and through the effector assembly, with the effector assembly in the first relationship, to expose the tissue sample to the atmosphere for the examination of the tissue sample.

75. In an actuating assembly as set forth in claim 72, the lumen in the tube having a long axis, the second means including a rotary member disposed in the lumen in the flexible tube to envelope the tissue sample and including fourth means disposed in the lumen in the flexible tube for rotating the rotary member and including fifth means disposed in the lumen in the flexible tube for translating the rotary movement of the rotary member to a movement of the tissue sample into the tube along the long axis of the tube.

76. In an actuating assembly as set forth in claim 75, the third means being operative to move the rotary member through the lumen in the flexible tube along the long axis of the lumen and through the effector assembly, with the effector assembly in the first relationship, to expose the tissue sample to the atmosphere for the examination of the tissue sample.

77. In an actuating assembly as set forth in claim 72, the effector assembly including a pair of jaws pivotable relative to each other between open and closed positions, the effector assembly providing the first relationship in the open position and the second relationship in the closed position, and the second means including means for pivoting the jaws to the open relationship at first particular times and to the closed relationship at second particular times different from the first particular times.

78. In an actuating assembly as set forth in claim 76, the effector assembly including a pair of jaws pivotable relative to each other between open and closed positions, the effector assembly providing the first relationship in the open position and the second relationship in the closed position, and the second means including means for pivoting the jaws to the open relationship at first particular times and to the closed relationship at second particular times different from the first particular times.

79. In an actuating assembly for obtaining a tissue sample from a wall defining a cavity in a patient and for retaining the tissue sample, a flexible tube having a lumen extending through the flexible tube, the flexible tube being constructed to be variably positioned in the cavity in the patient, an effector assembly having first and second operative relationships and operative in the first relationship to accept tissue from the wall of the cavity and operative in the second relationship to remove and retain a tissue sample in the effector assembly, first means operatively coupled to the effector assembly for providing a controlled operation of the effector assembly in the first and second relationships, second means for obtaining a transfer to the atmosphere of the tissue sample in the lumen in the flexible tube, and third means for providing a controlled bending of the flexible tube while the tissue sample is in the lumen in the flexible tube.

80. In an actuating assembly as set forth in claim 79, the effector assembly being operative in the first relationship during the transfer to the atmosphere of the tissue and sample in the lumen in the flexible tube.

81. In an actuating assembly as set forth in claim 79, the second means including fourth means for retaining the tissue sample in the lumen in the flexible tube and including fifth means for moving the fourth means to the atmosphere through the lumen in the flexible tube and through the effector assembly with the effector assembly in the first relationship.

82. In an actuating assembly as set forth in claim 81, the fourth means including a helical coil enveloping the tissue sample in the lumen in the flexible tube, and sixth means for providing a transfer of the tissue sample into the lumen in the flexible tube with the effector assembly in the second operative relationship, the sixth means including the helical coil and including seventh means for rotating the helical coil and including eighth means for translating the rotation of the helical coil into a directional movement of the tissue sample into the lumen in the flexible tube.

83. In an actuating assembly as set forth in claim 79, the lumen in the flexible tube having a long axis, the third means including fourth means movable along the long axis of the flexible tube for producing a tensile force on the flexible tube in the direction of the long axis and including fifth means disposed in the flexible tube at a particular side of the flexible tube for restricting the stretching of the flexible tube at such side to obtain a bending in a direction toward opposite the particular side.

84. In an actuating assembly as set forth in claim 79, the effector assembly including a pair of jaws pivotable relative to each other between open and closed positions, the jaws providing the first relationship in the open position and providing the second relationship in the closed position, the first means being operative to pivot the jaws to the open position at first particular times and to pivot the jaws to the closed position at second particular times different from the first particular times.

85. In an actuating assembly as set forth in claim 81, the lumen in the flexible tube having a long axis, the third means including sixth means movable along the long axis of the flexible tube for producing a tensile force on the tube in the direction of the long axis and including seventh means disposed in the flexible tube at a particular side of the flexible tube for restricting the stretching of the flexible tube at such side to obtain bending in a direction toward the particular side, the effector assembly including a pair of jaws pivotable relative to each other between open and closed positions, the jaws providing the first relationship in the open position and providing the second relationship in the closed position, the first means being operative to pivot the jaws to the open position at first particular times and to pivot the jaws to the closed position at second particular times different from the first particular times.

86. In an actuating assembly as set forth in claim 79, the lumen in the tube having a long axis, the third means including seventh means movable along the long axis of the flexible tube for producing a tensile force on the flexible tube in the direction of the long axis and including fifth means disposed in the flexible tube at a particular side of the flexible tube for restricting the stretching of the flexible tube at such side to obtain bending in a direction toward the particular side, the effector assembly including a pair of jaws pivotable relative to each other between open and closed positions, the jaws providing the first relationship in the open position and providing the second relationship in the closed position, the first means being operative to pivot the jaws to the open position at first particular times and to pivot the jaws to the closed position at second particular times different from the first particular times.

87. In an actuating assembly for obtaining a tissue sample from a wall defining a cavity in a patient and for retaining the tissue sample, a flexible tube having a lumen extending through the flexible tube, the flexible tube being constructed to be variably positioned in the cavity in the patient, an effector assembly having first and second operative relationships and operative in the first relationship to accept tissue from the wall of the cavity and operative in the second relationship to remove and retain such tissue sample in the effector assembly, first means disposed in the tube and operatively coupled to the effector assembly for obtaining a controlled operation of the effector assembly in the first and second relationships, second means disposed externally of the flexible tube and operatively coupled to the first means for obtaining the operation by the first means of the effector assembly in the first and second operative relationships, third means disposed in the lumen in the flexible tube for operating upon the tissue sample in the effector assembly to obtain a transfer of the tissue sample from the lumen in the tube to the atmosphere, fourth means disposed externally of the flexible tube and operatively coupled to the third means for obtaining a transfer by the third means of the tissue sample from the lumen in the flexible tube to the atmosphere, fifth means for providing a controlled bending of the flexible tube, and sixth means disposed externally of the flexible tube and operatively coupled to the fifth means for obtaining a controlled bending of the flexible tube by the fifth means.

88. In an actuating assembly as set forth in claim 87, the flexible tube being transparent in positions between the position of the controlled bending of the tube and the effector assembly to provide for the visual viewing of the tissue sample in the flexible tube.

89. In an actuating assembly as set forth in claim 87, the lumen in the flexible tube having a long axis, the fifth means including seventh means movable along the long axis of the flexible tube for producing a tensile force on the tube in the direction of the long axis and including eighth means disposed in the flexible tube at a particular side of the tube for restricting the stretching of the flexible tube at such side to obtain bending of the flexible tube in a direction toward the particular axis.

90. In an actuating assembly as set forth in claim 87, the third means including a member for enveloping the tissue sample in the lumen in the flexible tube, and the fourth means being operative to move the enveloping member through the lumen in the flexible tube and through the effector assembly with the effector assembly in the first relationship to expose the enveloping member to the atmosphere.

91. In an actuating assembly as set forth in claim 87, the effector assembly including a pair of jaws pivotable relative to each other between open and closed positions, the jaws providing the first relationship in the open position and providing the second relationship in the closed position, the first means being operatively coupled to the jaws to pivot the jaws between the open and closed positions.

92. In an actuating assembly as set forth in claim 87, the third means including a member for enveloping the tissue sample in the lumen in the flexible tube, and the fourth means being operative to move the enveloping member through the lumen in the flexible tube and through the effector assembly with the effector assembly in the first relationship to expose the effector assembly to the atmosphere, the effector assembly including a pair of jaws pivotable relative to each other between open and closed positions, the jaws providing the first relationship in the open position and providing the second relationship in the closed position, the first means being operatively coupled to the jaws to pivot the jaws between the open and closed positions.

* * * * *